US012774990B2

(12) United States Patent
Jannesari Ladani

(10) Patent No.: US 12,774,990 B2
(45) Date of Patent: Oct. 27, 2026

(54) SYSTEMS AND METHODS FOR DETECTION OF MICRON-SCALE INHOMOGENEITIES USING ULTRASOUND

(71) Applicant: Arizona Board of Regents on behalf of Arizona State University, Scottsdale, AZ (US)

(72) Inventor: Leila Jannesari Ladani, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 268 days.

(21) Appl. No.: 18/694,230

(22) PCT Filed: Oct. 4, 2022

(86) PCT No.: PCT/US2022/077518

§ 371 (c)(1),
(2) Date: Mar. 21, 2024

(87) PCT Pub. No.: WO2023/060070

PCT Pub. Date: Apr. 13, 2023

(65) Prior Publication Data

US 2024/0402131 A1 Dec. 5, 2024

Related U.S. Application Data

(60) Provisional application No. 63/251,865, filed on Oct. 4, 2021.

(51) Int. Cl.
*G01N 29/04* (2006.01)
*G01N 29/12* (2006.01)
(Continued)

(52) U.S. Cl.
CPC ........... *G01N 29/043* (2013.01); *G01N 29/12* (2013.01); *G01N 29/348* (2013.01); *G01N 29/46* (2013.01); *G01N 33/4833* (2013.01)

(58) Field of Classification Search
CPC .... G01N 29/043; G01N 29/12; G01N 29/348; G01N 29/46; G01N 33/4833
See application file for complete search history.

(56) References Cited

U.S. PATENT DOCUMENTS 5,635,619 A * 6/1997 Udpa .................... B06B 1/0284 73/DIG. 1
2002/0177769 A1* 11/2002 Orbach ................. A61B 5/418 600/431
(Continued)

FOREIGN PATENT DOCUMENTS

CN 101044990 B * 11/2011 ............... A61N 5/00
CN 102905732 A * 1/2013 ........... A61L 15/425
(Continued)

*Primary Examiner* — Chico A Foxx
(74) *Attorney, Agent, or Firm* — Riverside Law LLP

(57) ABSTRACT

A system for detecting one or more inhomogeneities in a sample (e.g., biological tissue) is disclosed. The system comprises a pulser-receiver, first and second ultrasound transducers, and a processor. The first ultrasound transducer may generate a high frequency ultrasound (HFU) signal in response to electrical pulses from the pulser-receiver, whereby the HFU signal is scattered through the sample and received by the second ultrasound transducer. An electronic signal indicative of the scattered HFU signal is received by the processor via the pulser-receiver. The signal is windowed, converted to frequency domain via fast Fourier transform, and assessed for peak quantity and peak frequencies within resonant frequency bands associated with the inhomogeneities. Inhomogeneities in the sample may be indicated by a peak quantity greater than a baseline value associated with homogenous samples and/or peaks at new
(Continued)

200 frequencies with respect to a baseline spectrum associated with homogenous samples.

19 Claims, 15 Drawing Sheets

(51) Int. Cl.

*G01N 29/34* (2006.01)
*G01N 29/46* (2006.01)
*G01N 33/483* (2006.01)

(56) References Cited

U.S. PATENT DOCUMENTS

| | | | |
|---|---|---|---|
| 2003/0045794 A1 | 3/2003 | Bae | |
| 2005/0160817 A1 | 7/2005 | Clement | |
| 2007/0006651 A1 | 1/2007 | Kruger | |
| 2009/0105591 A1 | 4/2009 | Christopher | |
| 2009/0281422 A1* | 11/2009 | Salama | A61B 5/4312 600/430 |
| 2013/0269441 A1 | 10/2013 | Doyle | |
| 2016/0045184 A1 | 2/2016 | Courtney | |
| 2018/0309529 A1 | 10/2018 | Liu | |
| 2019/0004014 A1* | 1/2019 | Webster | G01N 29/4427 |
| 2022/0096857 A1* | 3/2022 | Prebeg | A61N 1/44 |
| 2023/0097973 A1* | 3/2023 | Rajagopal | A61B 5/022 600/438 |

FOREIGN PATENT DOCUMENTS

| | | | | |
|---|---|---|---|---|
| CN | 103109186 A | * | 5/2013 | G01N 27/26 |
| CN | 103314294 A | * | 9/2013 | G01N 29/02 |
| CN | 111150424 A | * | 5/2020 | A61B 8/4483 |
| WO | WO-2017129415 A1 | * | 8/2017 | H04R 17/00 |

* cited by examiner

Flow chart for the experimental determination of peak density.

Peak densities density relationship with size and number of scatterers (inhomogeneities)

Magnitude of the scattered field for two beads configurations at two different frequencies

SYSTEMS AND METHODS FOR DETECTION OF MICRON-SCALE INHOMOGENEITIES USING ULTRASOUND

CROSS-REFERENCE TO RELATED APPLICATIONS

This application is a U.S. national phase application filed under 35 U.S.C. § 371 claiming benefit to International Patent Application No. PCT/US2022/077518, filed Oct. 4, 2022, which is entitled to priority of U.S. provisional application No. 63/251,865 filed on Oct. 4, 2021, the contents of which are each incorporated by reference herein in their entirety.

TECHNICAL FIELD

The present disclosure relates generally to methods, systems, and apparatuses related to detection of inhomogeneities in a medium. More particularly, the present disclosure relates to the use of high frequency ultrasound to detect micron-scale inhomogeneities in a sample in a non-destructive manner. The disclosed techniques may be applied to, for example, detection of cancerous cells in a tissue sample, e.g., breast tissue. The disclosed techniques may also be applied to other organic substances and/or to synthetic materials (e.g., polymers) to assess purity and/or uniformity.

BACKGROUND

In various applications, it may be necessary and/or beneficial to assess the composition of a material to determine the uniformity thereof and/or to detect the presence or absence of one or more components. For example, in manufacturing applications, it may be useful to assess the uniformity of a material to ensure satisfaction of quality standards and/or tolerances. In another example, it may be useful to assess the purity of refined organic substances for medicinal, cosmetic, and/or other applications.

One of the major tools having the potential for rapidly assessing material samples is high frequency ultrasound (HFU), which may be used for assessing mechanical properties of various material. Ultrasound imaging is currently a widely used technology in some fields, e.g., assessment of soft tissue in medical applications for diagnosis and/or post-intervention evaluation of patients. Due to their shorter wavelength, high frequency ultrasound (HFU) is viable for use in stimulating or detecting smaller scale inhomogeneities, e.g., at the cellular level of biological tissues. However, while HFU beams can provide better resolution, they may be limited to assessing relatively thin samples because HFU beams progressively experience rapid attenuation. As such, current technologies are limited by their achievable lateral and axial resolution.

A particular application of interest is rapid assessment of cellular material to detect diseased cells, e.g., cancerous cells. Recent research into the mechano-biology of human cell continues to expand knowledge of the effects of mechanical stimuli on human cells. Cells may be exposed to different types of forces and stimuli and may respond to these forces through several different mechanisms (i.e., mechanotransduction). Understanding the mechano-biology of human cells may enable further study and/or diagnosis of biological conditions and/or disorders, including cancer. For example, research has shown many times that cancerous cells have different mechanical stiffness than the healthy cells. The link between cancer and biomechanics has been demonstrated to operate in multiple directions, with tumorigenesis remodeling the mechanical environment of the surrounding tissue and the mechanical environment of the surrounding tissue directly influencing tumor development in the epithelium. Cancer can also often be identified by its morphology; as opposed to normal cells which have ellipsoid shape with smooth outlines nuclei, many cancer cells are easily identifiable by increased nuclear size, irregular nuclear contours, and disturbed chromatin distribution, which may dominate the overall cellular mechanical response. Accordingly, these changes in the properties of cancer cells can potentially be exploited to detect cancer. However, the behaviors and essential processes that form the basis of cell biomechanical responses are still obscure and/or only partially understood.

In clinical settings, it may often be important and/or necessary to detect cancer at the cellular resolution. For example, while a surgical excision of breast cancer lumps is an effective option for removing breast cancer, there is a possibility that cancer remains in the tissue margins and causes re-growth and/or metastasis. Currently, the tissue may be assessed through mammography and/or magnetic resonance imaging (MRI) to plan a complete excision of the cancer tissue. However, there is a high likelihood of inaccurate assessment because the imaging is performed pre-operatively and does not account for later developments and/or a degree of inaccuracy in surgical procedures. Tissue may also be assessed through frozen section analysis, touch preparation cytology, electromagnetic probes, and/or optical imaging. However, these techniques may be labor intensive, time-consuming, and may need to be performed post-operatively. As a result, a second intensive re-excision procedure may need to be performed if cancer is detected. The current solutions may also create further difficulties such as inaccuracy due to artifacts, limitations on the amount of tissue capable of being tested, and/or additional time or steps required for testing. As such, the medical field would benefit from an effective solution for detecting cancer at the margins of the excised tissue.

Accordingly, it would be advantageous to have a system for detecting inhomogeneities in a sample material in a quick and simplified manner. For example, it would be advantageous to have a system for intra-operatively detecting cancer cells amongst a healthy biological tissue (e.g., after excision of a cancer mass) in a time- and cost-efficient manner. Further, as described herein, various other fields may benefit from systems capable of detecting inhomogeneities in a sample material, including but not limited to synthetic and refined materials.

SUMMARY

Some embodiments of the invention disclosed herein are set forth below, and any combination of these embodiments (or portions thereof) may be made to define another embodiment.

A system for detecting one or more inhomogeneities in a material sample is provided. In some embodiments, the one or more inhomogeneities have one or more predetermined resonant frequencies. The system comprises: a pulser-receiver configured to generate one or more electrical pulses; a first ultrasound transducer configured to be arranged on a first side of the material sample, wherein the first ultrasound transducer is configured to generate one or more high frequency ultrasound (HFU) signals in response to receiving the one or more electrical pulses, wherein the one or more HFU signals propagate through the material sample and undergo scattering therein; a second ultrasound transducer configured to be arranged on a second side of the material sample opposite the first side, wherein the second ultrasound transducer is configured to receive the one or more scattered HFU signals from the material sample and transmit one or more electronic signals indicative of the one or more scattered HFU signals to the pulser-receiver; a processor; and a non-transitory, computer-readable medium storing instructions that, when executed, cause the processor to: receive the one or more electronic signals from the pulser-receiver, generate a windowed signal based on the one or more electronic signals by applying a window function, convert the windowed signal to frequency domain via fast Fourier transform, determine, for the converted signal, a peak quantity within one or more resonant frequency bands associated with the one or more predetermined resonant frequencies, and compare the peak quantity to a baseline value, wherein a peak quantity greater than the baseline value is indicative of a presence of the one or more inhomogeneities in the material sample.

According to some embodiments, the first ultrasound transducer is in electrical communication with the pulser-receiver via a first ultrasound transmission line and the second ultrasound transducer is in electrical communication with the pulser-receiver via a second ultrasound transmission line.

According to some embodiments, the HFU signal comprises a frequency bandwidth between about 0.5 MHz and about 100 MHz.

According to some embodiments, in response to receiving the one or more electrical pulses, the first ultrasound transducer is configured to oscillate at a frequency bandwidth between about 0.5 MHz and about 100 MHz, thereby generating the HFU signal.

According to some embodiments, the system further comprises an oscilloscope in electrical communication with the pulser-receiver, wherein the oscilloscope is configured to receive the electronic signal from pulser-receive and digitize the electronic signal, wherein instructions that cause the processor to receive the electronic signal from the pulser-receiver comprise instructions that, when executed, cause the processor to receive the digitized electronic signal from the pulser-receiver via the oscilloscope.

According to some embodiments, the instructions that cause the processor to window the electronic signal comprise instructions that, when executed, cause the processor to: isolate an interval of the electronic signal; and multiply the interval of the electronic signal by the window function, thereby generating a tapered waveform of the interval. According to additional embodiments, the window function is a Tukey window function.

According to some embodiments, the instructions that cause the processor to determine a peak quantity of the converted signal comprise instructions that, when executed, cause the processor to: calibrate the converted signal; differentiate the calibrated signal; and count zero-crossings in the differentiated signal within the one or more resonant frequency bands to determine the peak quantity. According to additional embodiments, the instructions that cause the processor to calibrate the converted signal comprise instructions that, when executed, cause the processor to divide the converted signal by a reference spectrum. According to further embodiments, the reference spectrum is associated with an ultrasound signal transmitted from the first ultrasound transducer to the second ultrasound transducer in the absence of the material sample.

According to some embodiments, the baseline value is determined based on one or more of historical data, empirical data, and a simulation based on one or more known characteristics of the material sample.

According to some embodiments, the one or more predetermined resonant frequencies are predetermined based on one or more of historical data, empirical data, and a simulation based on one or more known characteristics of the one or more inhomogeneities. According to additional embodiments, the one or more known characteristics comprise one or more of a size, a shape, and a mechanical property of the one or more inhomogeneities.

According to some embodiments, the HFU signal comprises the one or more predetermined resonant frequencies.

According to some embodiments, the first ultrasound transducer and the second ultrasound transducer are arranged in a pitch-catch arrangement.

According to some embodiments, the material sample comprises a biological tissue sample and the one or more inhomogeneities comprise one or more cells exhibiting a condition. According to additional embodiments, the condition is cancer.

According to some embodiments, the material sample comprises a breast tissue sample and the one or more inhomogeneities comprise one or more breast cancer cells. According to additional embodiments, the breast tissue sample is a tissue margin at a breast cancer excision site.

According to some embodiments, the one or more electrical pulses comprise a plurality of electrical pulses; the one or more HFU signals comprise a plurality of HFU signals; the one or more scattered HFU signals comprise a plurality of scattered HFU signals; and the one or more electronic signals comprise a plurality of electrical signals. According to additional embodiments, the instructions, when executed, further cause the processor to average the plurality of electronic signals to obtain an averaged signal, wherein the windowed signal is based on the averaged signal.

According to some embodiments, the instructions, when executed, further cause the processor to control the pulser-receiver to generate the one or more electrical pulses.

According to some embodiments, the system further comprises an amplifier in electrical communication with the pulser-receiver and configured to amplify the one or more electronic signals, wherein the one or more electronic signals received by the processor from the pulser-receiver comprise amplified electronic signals received from the pulser-receiver via the amplifier.

According to some embodiments, the one or more resonant frequency bands comprise a resonant frequency band for each of the one or more predetermined resonant frequencies, wherein each frequency band comprises a frequency bandwidth including the predetermined resonant frequency.

A system for detecting one or more inhomogeneities in a material sample is provided. In some embodiments, the one or more inhomogeneities have one or more predetermined resonant frequencies. The system comprises: a pulser-receiver configured to generate one or more electrical pulses; a first ultrasound transducer configured to be arranged on a first side of the material sample, wherein the first ultrasound transducer is configured to generate one or more high frequency ultrasound (HFU) signals in response to receiving the one or more electrical pulses, wherein the one or more HFU signals propagate through the material sample and undergo scattering therein; a second ultrasound transducer configured to be arranged on a second side of the material sample opposite the first side, wherein the second ultrasound transducer is configured to receive the one or more scattered HFU signals from the material sample and transmit one or more electronic signals indicative of the one or more scattered HFU signals to the pulser-receiver; a processor; and a non-transitory, computer-readable medium storing instructions that, when executed, cause the processor to: receive the one or more electronic signals from the pulser-receiver, generate a windowed signal based on the one or more electronic signals by applying a window function, convert the windowed signal to frequency domain via fast Fourier transform, determine, for the converted signal, one or more peak frequencies within one or more resonant frequency bands associated with the one or more predetermined resonant frequencies, and compare the one or more peak frequencies to a baseline spectrum, wherein a peak frequency present in the converted signal and absent in the baseline spectrum is indicative of a presence of the one or more inhomogeneities in the material sample.

A method for detecting one or more inhomogeneities in a material sample is provided. In some embodiments, the one or more inhomogeneities have one or more predetermined resonant frequencies. The method comprises: transmitting, by a pulser-receiver, one or more electrical pulses to a first ultrasound transducer arranged on a first side of the material sample; generating, by the first ultrasound transducer, one or more one or more high frequency ultrasound (HFU) signals in response to the one or more electrical pulses, wherein the HFU signals propagate through the material sample and undergo scattering; receiving, by a second ultrasound transducer a second side of the material sample opposite the first side, the one or more scattered HFU signals from the material sample; transmitting, by the second ultrasound transducer, one or more electronic signals indicative of the one or more scattered HFU signals to a processor via the pulser-receiver; generating, by the processor, a windowed signal based on the one or more electronic signals by applying a window function; converting the windowed signal to frequency domain via fast Fourier transform; determining, for the converted signal, a peak quantity within one or more resonant frequency bands associated with the one or more predetermined resonant frequencies; and comparing the peak quantity to a baseline value, wherein a peak quantity greater than the baseline value is indicative of a presence of the one or more inhomogeneities in the material sample.

A method for detecting one or more inhomogeneities in a material sample is provided. In some embodiments, the one or more inhomogeneities have one or more predetermined resonant frequencies. The method comprises: transmitting, by a pulser-receiver, one or more electrical pulses to a first ultrasound transducer arranged on a first side of the material sample; generating, by the first ultrasound transducer, one or more one or more high frequency ultrasound (HFU) signals in response to the one or more electrical pulses, wherein the HFU signals propagate through the material sample and undergo scattering; receiving, by a second ultrasound transducer a second side of the material sample opposite the first side, the one or more scattered HFU signals from the material sample; transmitting, by the second ultrasound transducer, one or more electronic signals indicative of the one or more scattered HFU signals to a processor via the pulser-receiver; generating, by the processor, a windowed signal based on the one or more electronic signals by applying a window function; converting the windowed signal to frequency domain via fast Fourier transform; determining, for the converted signal, one or more peak frequencies within one or more resonant frequency bands associated with the one or more predetermined resonant frequencies; and comparing the one or more peak frequencies to a baseline spectrum, wherein a peak frequency present in the converted signal and absent in the baseline spectrum is indicative of a presence of the one or more inhomogeneities in the material sample.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. Various aspects of at least one example are discussed below with reference to the accompanying drawings, which are not intended to be drawn to scale. In the drawings.

DETAILED DESCRIPTION

Figure 1:
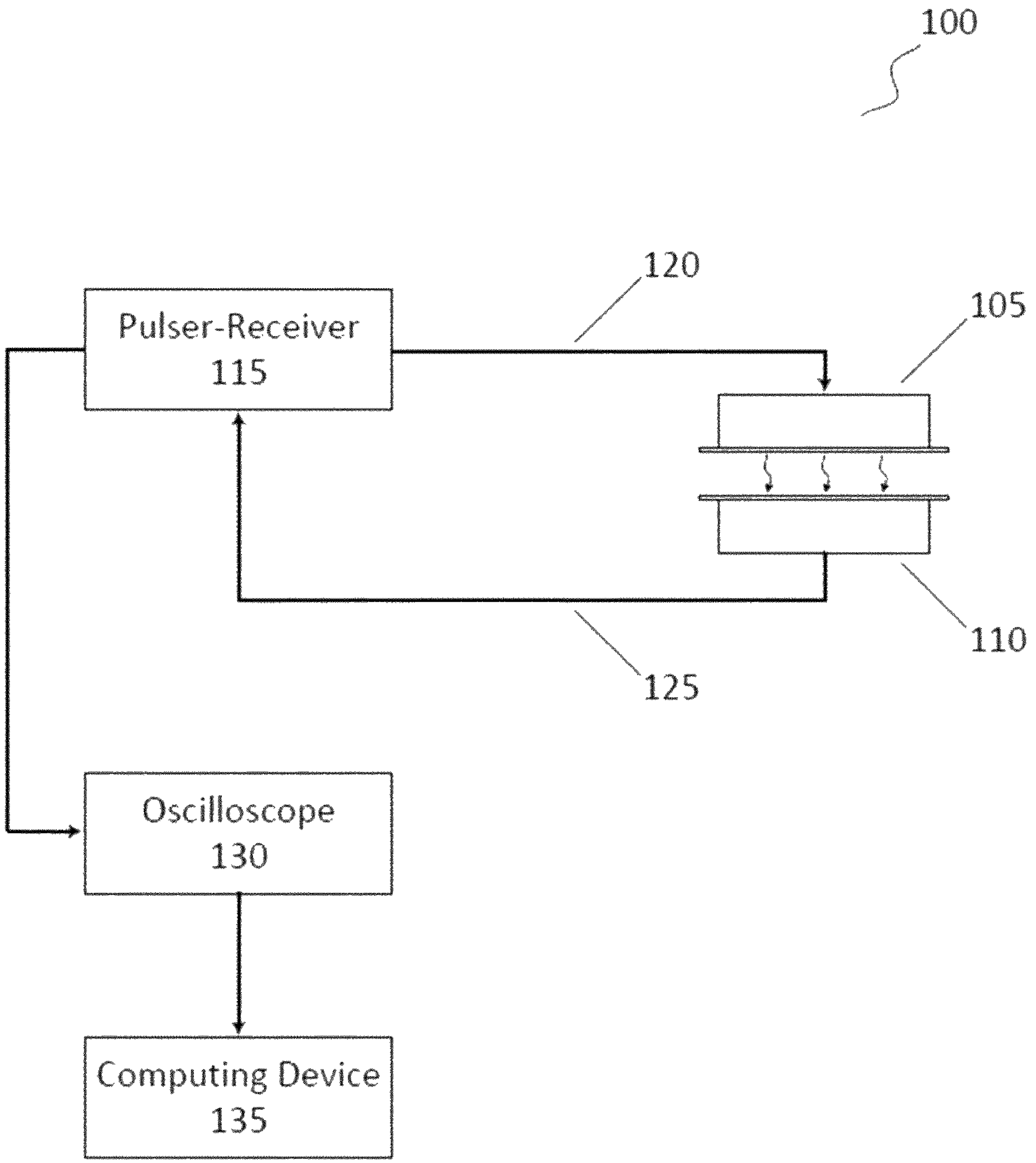
FIG. 1 depicts an exemplary diagram of a system for detecting material inhomogeneities in a sample in accordance with an embodiment.

This disclosure is not limited to the particular systems, devices and methods described, as these may vary. The terminology used in the description is for the purpose of describing the particular versions or embodiments only, and is not intended to limit the scope. Such aspects of the disclosure be embodied in many different forms; rather, these embodiments are provided so that this disclosure will be thorough and complete, and will fully convey its scope to those skilled in the art.

As used in this document, the singular forms "a," "an," and "the" include plural references unless the context clearly dictates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein are intended as encompassing each intervening value between the upper and lower limit of that range and any other stated or intervening value in that stated range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells as well as the range of values greater than or equal to 1 cell and less than or equal to 3 cells. Similarly, a group having 1-5 cells refers to groups having 1, 2, 3, 4, or 5 cells, as well as the range of values greater than or equal to 1 cell and less than or equal to 5 cells, and so forth.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, structures, or groups thereof, or any members of a claimed group, less than the full measure of this disclosure can be claimed for any reason.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art. Where the context of the disclosure indicates otherwise, or is inconsistent with such an interpretation, the above-stated interpretation may be modified as would be readily apparent to a person skilled in the art. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). Further, the transitional term "comprising," which is synonymous with "including," "containing," or "characterized by," is inclusive or open-ended and does not exclude additional, unrecited elements or method steps. While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "patient" and "subject" are interchangeable and refer to any living organism which contains neural tissue. As such, the terms "patient" and "subject" may include, but are not limited to, any non-human mammal, primate or human. A subject can be a mammal such as a primate, for example, a human. The term "subject" includes domesticated animals (e.g., cats, dogs, etc.); livestock (e.g., cattle, horses, swine, sheep, goats, etc.), and laboratory animals (e.g., mice, rabbits, rats, gerbils, guinea pigs, possums, etc.). A patient or subject may be an adult, child or infant.

The term "tissue" refers to any aggregation of similarly specialized cells which are united in the performance of a particular function.

The term "disorder" is used in this disclosure to mean, and is used interchangeably with, the terms "disease," "condition," or "illness," unless otherwise indicated.

The term "high frequency ultrasound" or "HFU" is used to refer to ultrasound waves having a frequency between about 0.5 MHz and about 100 MHz, unless otherwise indicated.

The term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

Throughout this disclosure, various patents, patent applications and publications are referenced. The disclosures of these patents, patent applications and publications are incorporated into this disclosure by reference in their entireties in order to more fully describe the state of the art as known to those skilled therein as of the date of this disclosure. This disclosure will govern in the instance that there is any inconsistency between the patents, patent applications and publications cited and this disclosure.

As discussed herein, recent investigations of the difference between acoustic impedance of healthy and cancerous breast cancer cells at high frequencies has indicated a slight difference in impedance values between normal and cancerous cells. As the sound-wave frequency is increased and the size of the scatterers within a specimen is reduced, the scattering regime shifts from Specular to Scattering to Rayleigh regime. In addition to frequency and scatterer size, such scattering behavior depends on the characteristics of these inhomogeneities including shape and visco-elastic behavior of the scatterer and their surrounding media. It is suspected that if the sound wave's frequency matches the scatterer's natural frequency, sound waves can resonate these scatterers and cause an increase in amplitude at certain frequencies. These deviations in the sound wave can be observed in the frequency domain spectrum of the signal received from the material as peaks appearing at or near these resonant frequencies.

It has been suggested that HFU may be useful in detecting certain types of cancers and much literature has focused on cancer cell behavior in the HFU domain. However, the link between mechanics of wave propagation and how the impact of acoustic properties of the individual cells on signal scattering behavior is largely missing. Very few studies have been conducted on use of HFU in conjunction with tissues at the cellular level for understanding the biomechanical response of cells. Furthermore, challenges exist because the natural resonant frequencies of cancer cells are unknown and the complex mechano-biology of biological systems has not been studied in detail and clearly defined. For example, visco-elastic behavior of the surrounding tissue and damping of acoustic vibration can create challenges in implementing this resonance. Additional complexities arise due to natural inhomogeneities of healthy tissues. For example, different types of cells including epithelial, extracellular matrix protein, adipose tissue (adipocytes), and the like may appear as inhomogeneities. Therefore, it is necessary to understand the biomechanical phenomenon in a manner that allows focusing detection on specific Accordingly, it would be advantageous to have a tool for using HFU to manipulate and/or detect specific types of biological cells. Ideally, HFU could be used to detect cancer cells or cells exhibiting other disorders among a sample of healthy biological tissues. Such a technology would facilitate early detection of cancer as well as screening of margin tissue after cancer mass excision.

System for Detection of Material Inhomogeneities

FIG. 1 depicts an exemplary diagram of a system for detecting material inhomogeneities in a sample in accordance with an embodiment. For example, the sample may be a sample of biological tissue. In one embodiment, the biological tissue is breast tissue. However, it should be understood that the system 100 may be utilized to assess various types of materials to detect inhomogeneities therein. The material may be any material having a relatively consistent or homogeneous makeup and/or suspected inhomogeneities with foreseeable resonant frequencies and/or biomechanical characteristics as described herein.

In some embodiments, the system 100 may be utilized as described herein to detect inhomogeneities in a tissue of a patient's anatomy. In some embodiments, the inhomogeneities may be cancer cells within a tissue. For example, the cancer cells may be breast cancer cells within a breast tissue (e.g., a pre-operative tissue and/or a tissue margin of an excised tissue). However, the cancer cells may be any type of cancer cells as would be apparent to a person having an ordinary level of skill in the art. In some embodiments, the cancer cells may have distinct biomechanical properties from the surrounding healthy tissue and may thus be detected as inhomogeneities by the system 100. However, it should be understood that other types of tissue inhomogeneities may be detected by the system 100 as described herein. For example, the inhomogeneities may be fibrotic cells, fat cells, cells exhibiting another condition or disorder, and/or cells having distinct biomechanical properties from another portion of the sample due to any other cause as would be apparent to a person having an ordinary level of skill in the art.

As shown in FIG. 1, the system 100 comprises a first ultrasound transducer 105, a second ultrasound transducer 110, a pulser-receiver 115, an oscilloscope 130, and a computing device 135.

The ultrasound transducers 105/110 may be configured to receive a sample therebetween. For example, as shown in FIG. 1, the sample may be placed between the ultrasound transducers 105/110 to "sandwich" the sample therebetween. In some embodiments, the first ultrasound transducer 105 may be arranged and configured to contact a first side of the sample and the second ultrasound transducer 110 may be arranged and configured to contact a second side of the sample opposite the first side.

In some embodiments, coupling gel, coupling liquid, or another acoustic couplant as would be known to a person having an ordinary level of skill in the art may be utilized to reduce acoustic impedance at the interface between the ultrasound transducers 105/110 and the sample. Pockets of air, gases, vapors, or other materials between the ultrasound transducers 105/110 and the sample can alter the transmissivity of ultrasonic pulses. Accordingly, enhanced contact provides greater transmission of an emitted signal and/or a received signal. Accordingly, a coupling gel, coupling liquid, and/or another acoustic couplant may be applied to the contact surface of one or both of the ultrasound transducers 105/110 to improve transmission of ultrasonic wave pulses and reduce interference or distortion.

In some embodiments, the first ultrasound transducer 105 is configured to emit an ultrasound signal to the sample. In some embodiments, the first ultrasound transducer 105 is configured to emit a high frequency ultrasound (HFU) signal to the sample. In some embodiments, the ultrasound transducer 105 may be configured to emit an HFU signal with a bandwidth between about 0.5 MHz and about 100 MHz. In some embodiments, the ultrasound transducer 105 may be configured to emit an HFU signal with a bandwidth between about 0.5 MHz and about 25 MHz. In some embodiments, the ultrasound transducer 105 may be configured to emit an HFU signal with a bandwidth between about 0.5 MHz and about 50 MHz. In some embodiments, the ultrasound transducer 105 may be configured to emit an HFU signal with a bandwidth between about 0.5 MHz and about 75 MHz. In some embodiments, the ultrasound transducer 105 may be configured to emit an HFU signal with a bandwidth between about 25 MHz and about 50 MHz. In some embodiments, the ultrasound transducer 105 may be configured to emit an HFU signal with a bandwidth between about 25 MHz and about 75 MHz. In some embodiments, the ultrasound transducer 105 may be configured to emit an HFU signal with a bandwidth between about 25 MHz and about 100 MHz. In some embodiments, the ultrasound transducer 105 may be configured to emit an HFU signal with a bandwidth between about 50 MHz and about 75 MHz. In some embodiments, the ultrasound transducer 105 may be configured to emit an HFU signal with a bandwidth between about 50 MHz and about 100 MHz. In some embodiments, the ultrasound transducer 105 may be configured to emit an HFU signal with a bandwidth between about 75 MHz and about 100 MHz.

In some embodiments, the second ultrasound transducer 110 is configured to receive an ultrasound signal (e.g., a 'return' signal) from the sample. In some embodiments, the second ultrasound transducer 110 is configured to receive a scattered ultrasound return signal, i.e., the HFU signal that has been altered due to passing through the sample. For example, the first ultrasound transducer 105 and the second ultrasound transducer 110 may be arranged and configured for a pitch-catch mode. In a pitch-catch or direct through-transmission technique, the first ultrasound transducer 105 may emit an HFU signal to the sample that may pass therethrough and undergo scattering due to the material properties of the sample. The second ultrasound transducer 110 may subsequently receive the scattered ultrasound return signal from the sample.

In an alternate embodiment, a pulse-echo technique may be utilized. In a pulse-echo technique, an ultrasound transducer may emit an HFU signal to the sample that may pass therethrough and undergo scattering due to the material properties of the sample, including reflecting portions of the ultrasound signal back towards the ultrasound transducer. The ultrasound transducer may subsequently receive the back scattered ultrasound return signal (i.e., the 'echo' signal). Accordingly, one or both of the ultrasound transducers 105/110 may be arranged and configured for a pulse-echo mode, and as such, may transmit the HFU signal and detect the back scattered ultrasound return signal. In some embodiments, where the pulse-echo technique is utilized, the system may comprise a single ultrasound transducer. In some embodiments, where the pulse-echo technique is utilized, the system 100 may comprise two ultrasound transducers 105/110 operating redundantly, thereby providing additional data sets for validation and/or elimination of error or noise from the collected measurements. In some embodiments, the ultrasound transducers 105/110 may be configured to operate in either of a pitch-catch mode and a pulse-echo mode.

Referring once again to FIG. 1, the pulser-receiver 115 may be in electrical communication with the first ultrasound transducer 105 through a first ultrasound transmission line 120 configured to transmit a signal (e.g., an electronic signal) from the pulser-receiver 115 to the first ultrasound transducer 105. The pulser-receiver 115 may also be in electrical communication with the second ultrasound transducer 110 through a second ultrasound transmission line 125 configured to transmit a signal (e.g., an electronic signal) from the second ultrasound transducer 110 to the pulser-receiver 115. Accordingly, the pulser-receiver 115 may transmit an electronic signal (e.g., an applied AC voltage) to the first ultrasound transducer 105 that causes the first ultrasound transducer 105 to oscillate, thereby generating an HFU signal that is emitted to the sample. The HFU signal may pass through the sample and interact therewith in a manner that alters one or more portions of the HFU signal (e.g., by scattering as the HFU passes through the sample). For example, the HFU signal may be altered to increase a number of peaks (i.e., peaks on an axis of amplitude) at one or more frequencies as it passes through inhomogeneities in the sample as further described herein. Peaks may be indicative of scattering events as the HFU signal passes through the sample and may appear in the HFU signal as crests (i.e., positive amplitudes) and/or troughs or valleys (i.e., negative amplitudes). The second ultrasound transducer 110 may then receive the ultrasound return signal (i.e., the altered HFU signal at the other side of the sample and convert the ultrasound return signal to an electronic signal (e.g., an applied AC voltage) that is transmitted back to the pulser-receiver 115. It should be understood that while the present disclosure may refer to the pulser-receiver 115 and/or other downstream components of the system 100 (e.g., the ultrasound transmission lines 120/125, the amplifier, the oscilloscope 130, and/or the computing device 135) receiving an ultrasound return signal, such references herein should be interpreted as referring to the electronic signal corresponding to the ultrasound return signal (e.g., from the second ultrasound transducer 110) rather than the true ultrasound return signal, as would be apparent to a person having an ordinary level of skill in the art.

It should also be understood that the ultrasound transmission lines 120/125 may transmit signals in either or both directions as required for each of the various embodiments described herein. For example, where both ultrasound transducers 105/110 are operated in pulse-echo mode in parallel as described herein, each ultrasound transmission line 120/125 may both transmit signals to the corresponding ultrasound transducer and transmit signals therefrom to the pulser-receiver 115. In another example, each ultrasound transducer 105/110 may have a dedicated ultrasound receiving line for receiving signals from the pulser-receiver 115 and a dedicated ultrasound transmitting line for transmitting signals to the pulser-receiver 115.

In some embodiments, the pulser-receiver 115 may be replaced in the system 100 by a dedicated pulser and a dedicated receiver as separate components. For example, a pulser may be in electrical communication with the first ultrasound transducer 105 by an ultrasound transmission line (e.g., the first ultrasound transmission line 120) to transmit signals thereto, and a receiver may be in electrical communication with the second ultrasound transducer 110 by an ultrasound transmission line (e.g., the second ultrasound transmission line 125) to receive signals therefrom.

In some embodiments, the system 100 further comprises an amplifier. For example, the pulser-receiver 115 may be in electrical communication with an amplifier configured to amplify an electronic signal received by the pulser-receiver 115 from the second ultrasound transducer 110. For example, the amplifier may communicate with the pulser-receiver 115 via a transmission line or cable as would be known to a person having an ordinary level of skill in the art.

In some embodiments, the oscilloscope 130 is a digital oscilloscope. In some embodiments, the oscilloscope 130 may be in electrical communication with the pulser-receiver 115 to receive the electronic signal therefrom. For example, the oscilloscope 130 may communicate with the pulser-receiver 115 via a transmission line or cable as would be known to a person having an ordinary level of skill in the art to directly receive the electronic signal therefrom. In some embodiments, the oscilloscope 130 may communicate with the pulser-receiver 115 via the amplifier as described herein to receive the electronic signal. For example, the oscilloscope 130 may communicate with the amplifier via a transmission line or cable as would be known to a person having an ordinary level of skill in the art to receive the electronic signal. Accordingly, in some embodiments, the electronic signal received by the oscilloscope 130 may be an amplified electronic signal. The oscilloscope 130 may be used to digitize the electronic signal and/or display the ultrasound return signal visually. Accordingly, the electronic signal may be received by the pulser-receiver 115, amplified by the amplifier, and digitized by the oscilloscope 130.

In some embodiments, the oscilloscope 130 has a sample rate of about 1.25 gigasamples per second (GS/s). However, it should be understood that the sample rate of the oscilloscope 130 may vary based on the requirements of a particular application and/or a particular experimental setup. For example, the required sample rate may be affected by the Nyquist bandwidth, which is a function of the frequency content of a signal of interest. Accordingly, the oscilloscope 130 may have a sample rate of about 1 GS/s, about 1.5 GS/s, about 2 GS/s, about 2.5 GS/s, about 5 GS/s, about 10 GS/s, about 50 GS/s, about 100 GS/s, or individual values or ranges therebetween.

In some embodiments, the digitized electronic signal may be displayed to a user on a display of the oscilloscope 130. For example, the oscilloscope 130 may be used to monitor and/or visually assess the waveform of the ultrasound return signal received from the second ultrasound transducer 110.

In some embodiments, the oscilloscope 130 may be omitted such that the pulser-receiver 115 and/or amplifier communicate with the computing device 135. The computing device may be configured to perform any of the functions of the oscilloscope as described herein, including digitizing the electronic signal and/or displaying the ultrasound return signal visually via a display device.

Referring once again to FIG. 1, the computing device 135 may be in electrical communication with the oscilloscope 130 to receive the electronic signal (e.g., the amplified electronic signal) therefrom. For example, the computing device 135 may communicate with the oscilloscope 130 via a transmission line or cable as would be known to a person having an ordinary level of skill in the art to receive the electronic signal therefrom. However, in some embodiments, the oscilloscope 130 may be omitted from the system 100 and the computing device 135 may communicate directly with the pulser receiver 115 and/or amplifier to receive the electronic signal.

The computing device 135 may comprise one or more processors and a non-transitory, computer-readable storage medium storing instructions that, when executed, cause the one or more processors to perform a series of processing steps to detect one or more inhomogeneities in the sample. Inhomogeneities in a sample may exhibit different biomechanical properties (e.g., mechanical stiffness) than the remainder of the sample. For example, cancerous cells amongst healthy cells in a tissue sample have been shown to exhibit different mechanical stiffness than the healthy cells. Accordingly, by detecting one or more features of the ultrasound return signal indicative of the known biomechanical properties unique to inhomogeneities, the computing device 135 may detect the inhomogeneities in the sample. For example, as further described herein, the computing device 135 may detect an increased amplitude in the ultrasound return signal at or near one or more resonant frequencies associated with the inhomogeneities, thereby detecting the inhomogeneities in the sample. In some embodiments, detecting the inhomogeneities comprises determining the presence or absence of the inhomogeneities. In some embodiments, detecting the inhomogeneities comprises identifying the location of the inhomogeneities. It should be understood that because the detecting is based on known biomechanical properties and/or other physical properties of the inhomogeneities, the computing device 135 may be configured to detect a specific type of inhomogeneity while ignoring other types of inhomogeneities. For example, while a tissue sample may comprise cells exhibiting a variety of conditions or disorders, the computing device 135 may be configured to specifically detect cancerous cells amongst the tissue sample and distinguish the cancerous cells from healthy cells as well as scar tissue cells, calcifications, and/or other cells exhibiting conditions or disorders aside from cancer.

Figure 2A:
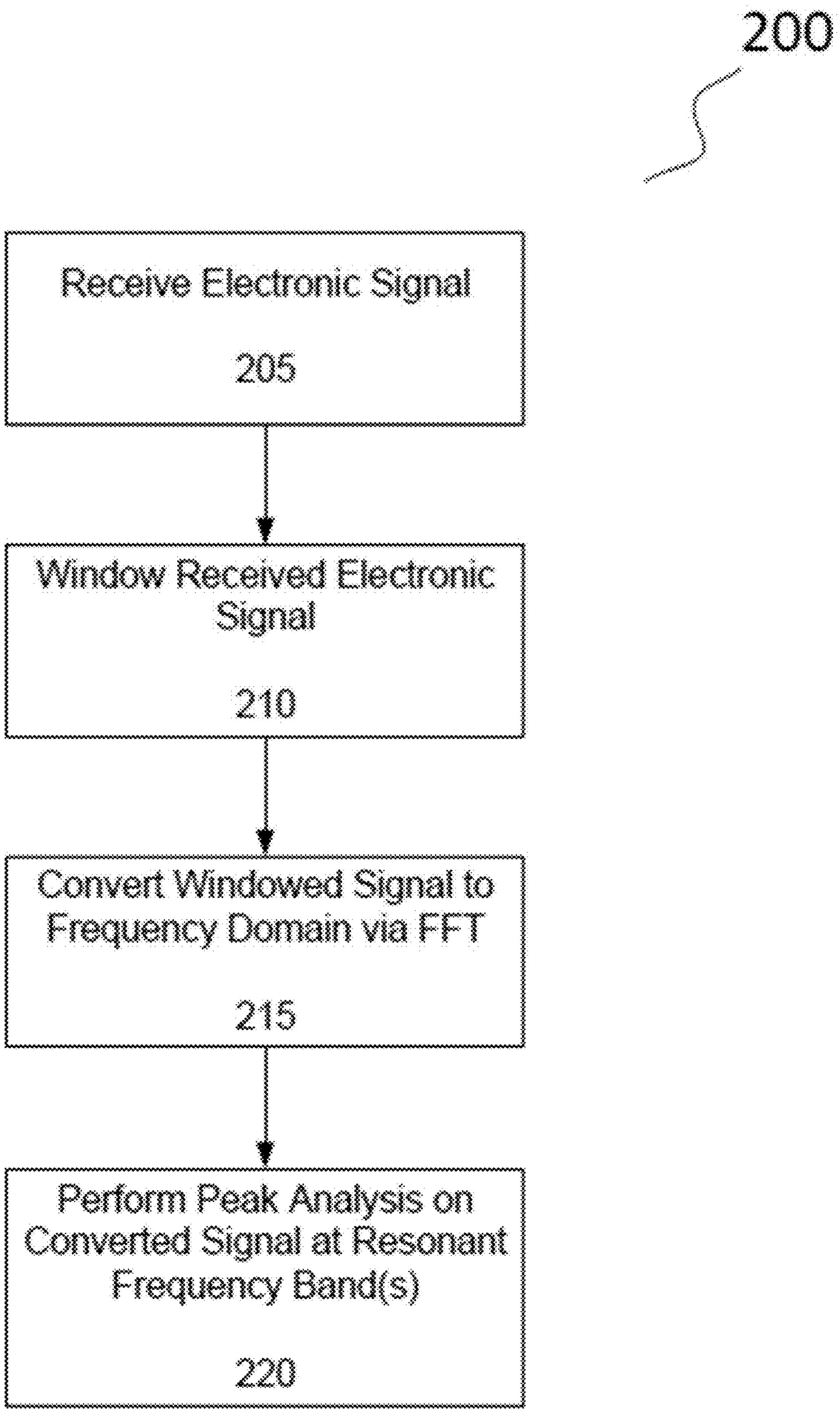
FIGS. 2A-2B depict illustrative flow diagrams of a computer-implemented method of detecting homogeneities in a sample in accordance with an embodiment.
Figure 2B:
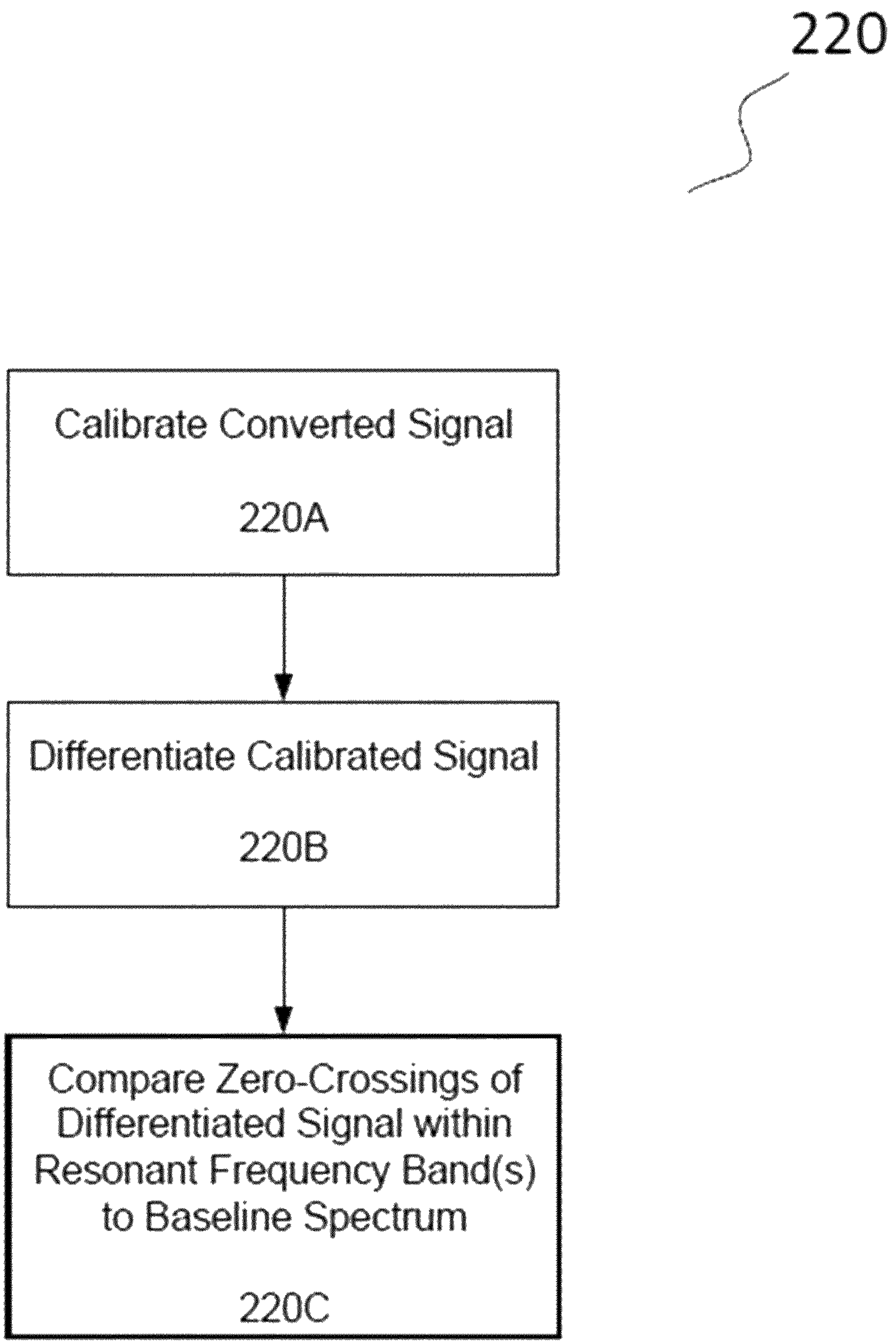

Referring now to FIGS. 2A-2B, an illustrative flow diagram of a computer-implemented method of detecting inhomogeneities in a sample is depicted in accordance with an embodiment. For example, the computer-implemented method 200 may be performed by a computing device such as computing device 135 using the system 100 of FIG. 1 as described hereinbelow. However, it should be understood that the method 200 may be performed by another processor or processors in communication with a system such as system 100 as would be apparent to a person having an ordinary level of skill in the art. For example, the computer-implemented method 200 may be performed by an oscilloscope such as the oscilloscope 130 of FIG. 1. In another example, a portion of the computer-implemented method 200 may be performed by an oscilloscope such as the oscilloscope 130 of FIG. 1 and the remainder of the computer-implemented method 200 may be performed by one or more processors such as the computing device 135 of FIG. 1.

As shown in FIG. 2A, the method 200 comprises receiving 205 an electronic signal indicative of an ultrasound return signal via a receiver, wherein the ultrasound return signal comprises an HFU signal transmitted through the sample. In some embodiments, the receiver is a pulser-receiver (e.g, pulser-receiver 115). In some embodiments, the ultrasound return signal may be received directly from the receiver. In some embodiments, the electronic signal is amplified by an amplifier and/or digitized by an oscilloscope (e.g., oscilloscope 130) prior to being received by the computing device as described herein. Accordingly, the computing device 135 may receive the electronic signal indirectly from the receiver with one or more intermediate components.

In some embodiments, the computing device 135 may further electrically communicate with the pulser-receiver 115 to control operation of the pulser-receiver 115. For example, the computing device 135 may instruct the pulser-receiver 115 to send a signal to the first ultrasound transducer 105, thereby initiating generation of an HFU signal to be transmitted through the sample. In another example, the computing device 135 may instruct the pulser-receiver 115 to send a series of pulses or signals to the first ultrasound transducer 105, thereby initiating generation of a series of HFU waves that are transmitted through the sample. In some embodiments, the computing device 135 may further electrically communicate with the amplifier, the oscilloscope 130, and/or additional components to control or modify functions thereof. However, it should also be understood that the pulser-receiver 115, amplifier, and/or oscilloscope 130 may operate independently or be controlled by a separate processor.

In some embodiments, wherein a series of HFU waves are generated by the first ultrasound transducer, the computing device 135 may receive 205 a series of signals indicative of a series of ultrasound return signals. For example, the pulser-receiver 115 may send a series of pulses to the first ultrasound transducer 105, thereby generating a series of HFU waves to be transmitted through the sample and resulting in a series of ultrasound return signals received 205 via the second ultrasound transducer 110. It should be understood that any number of pulses may be utilized as would be apparent to a person having an ordinary level of skill in the art. It should also be understood that because the pulses are substantially identical and unvaried, the resulting HFU waves are similarly substantially identical and unvaried. However, the noise present in the return signals may vary. Accordingly, in some embodiments, the computing device 135 may average the series of ultrasound return signals to obtain an average or composite ultrasound return signal to be used in subsequent processing steps. Averaging the ultrasound return signal may be beneficial to reduce noise in the represented ultrasound return signal for further calculations. Furthermore, it should be understood that the averaging of the series of ultrasound return signals may alternatively be performed by components of the system 100 upstream of the computing device 135, e.g., the oscilloscope 130.

Referring once again to FIG. 2A, the method 200 further comprises windowing 210 the electronic signal. The electronic signal may be windowed 210 in order to remove noise from the signal and provide the signal in a processed form suitable for peak analysis as further described herein. Accordingly, windowing 210 the signal may comprise isolating an interval of the electronic signal, e.g., an interval relevant to peak analysis, and applying a window function to the isolated interval of the electronic signal. In some embodiments the isolated interval may comprise a predetermined number of data points. For example, the signal may be windowed to about 1500 points. However, the signal may be windowed to about 500 points, about 1000 points, about 5000 points, or individual values or ranges therebetween based on the requirements of a particular application as would be known to a person having an ordinary level of skill in the art.

In some embodiments, applying the window function to the isolated interval comprises multiplying data points of the isolated interval by the window function values. In some embodiments, a Tukey window function or cosine-tapered window function may be utilized. However, various window functions known in the field of signal processing may be utilized herein. Accordingly, windowing 210 the signal may result in a windowed signal having reduced noise and a tapered waveform more suitable for peak detection and analysis.

Referring once again to FIG. 2A, the method 200 further comprises converting 215 the windowed signal from the time domain to the frequency domain using Fourier analysis. By applying a Fourier transform to the windowed signal, the windowed signal is represented as a function of frequency. Accordingly, the transformed signal may be a representation of a portion of the ultrasound return signal arranged according to the range of frequencies contained in the ultrasound return signal. In some embodiments, converting 215 the windowed signal comprises using a fast Fourier transform (FFT), i.e., an algorithm for efficiently computing a discrete Fourier transform (DFT) such as the windowed signal of the ultrasound return signal. In some embodiments, the Cooley-Tukey FFT algorithm may be utilized for converting 215 the windowed signal. However, any FFT algorithm as would be known to a person having an ordinary level of skill in the art may be utilized herein, including but not limited to the Prime-factor FFT algorithm, Bruun's FFT algorithm, the Rader-Brenner FFT algorithm, the Bluestein's FFT algorithm, the Winograd FFT algorithm, and the hexagonal FFT algorithm.

As shown in FIG. 2A, the method 200 further comprises performing 220 peak analysis for one or more resonant frequency bands of the converted signal to detect the one or more inhomogeneities in the sample. Generally, the peak analysis comprises identifying peaks of the calibrated signal within each resonant frequency band, determining the peak quantity (i.e., the number of peaks) within each band, and comparing the determined peak quantity of each band to a baseline quantity, i.e., an expected peak quantity in a sample without inhomogeneities. It should be noted that peaks may be indicative of scattering events as the HFU signal passes through the sample and may appear in the HFU signal as crests (i.e., positive amplitudes) and/or troughs or valleys (i.e., negative amplitudes). In some embodiments, a determined peak quantity that is elevated with respect to the baseline quantity for the band is indicative of an inhomogeneity. Furthermore, the peak analysis may comprise identifying peaks at new locations within the resonant frequency bands, i.e., peaks at frequencies where a peak is not present in the baseline spectrum. A new peak location may also be indicative of an inhomogeneity.

Each frequency band of interest may be a resonant frequency band, i.e., a range of frequencies at or near a predetermined resonant frequency of the inhomogeneities of interest. In some embodiments, the resonant frequency band comprises frequencies within about 1 MHz of the resonant frequency. However, the resonant frequency bands may comprise frequencies within about 0.1 MHz of the resonant frequency, about 0.5 MHz of the resonant frequency, about 1 MHz of the resonant frequency, about 2 MHz of the resonant frequency, about 5 MHz of the resonant frequency, or individual values or ranges therebetween.

The resonant frequencies of the inhomogeneities may be predetermined in a variety of manners. As described herein and generally understood by a person having an ordinary level of skill in the art, an inhomogeneity generally has distinct physical and/or biomechanical properties than the remainder of the sample and thus may have resonant frequencies specific to the characteristics of the inhomogeneity. For example, a specific category of inhomogeneities (e.g., cancerous cells in a cluster of a known size) may demonstrate resonant frequencies that remain substantially consistent across the category. Accordingly, the resonant frequencies of an inhomogeneity of interest may be predetermined based on the characteristics of the inhomogeneity. In some embodiments, simulations may be performed using known physical and/or biomechanical properties of an inhomogeneity of interest to calculate the resonant frequencies thereof. In some embodiments, design experiments may be performed to determine resonant frequencies using inhomogeneities of similar characteristics, e.g., a type of inhomogeneity, a shape of the inhomogeneity, a size of the inhomogeneity, and/or one or more mechanical properties of the inhomogeneity. In some embodiments, data from prior experiments and/or collections may be used to determine resonant frequencies in future assessments. For example, data from a plurality of collections for a plurality of types of inhomogeneities may be stored in a database and aggregated. In future assessments, the data may be accessed selectively, e.g., accessing data for prior collections involving inhomogeneities of similar characteristics, to determine resonant frequencies for a particular assessment. In some embodiments, machine learning may be applied to the database in order to improve and optimize prediction of resonant frequencies. As data is collected and databased over long periods of time, multiple samples, multiple patients, and so forth, the available data and thus the baseline or expected results, the resonant frequencies, and the features of the ultrasound signal associated with particular inhomogeneities may be further understood and better defined.

Accordingly, based on predetermined resonant frequencies, the peak analysis may be performed 220 by the computing device 135 through a series of steps. As shown in FIG. 2B, the peak analysis may comprise calibrating 220A the converted signal, differentiating 220B (i.e., taking the mathematical derivative of) the calibrated signal, and comparing 220C zero-crossings within each predetermined resonant frequency band to a baseline spectrum. In some embodiments, comparing 220C zero-crossings may comprise quantifying the zero-crossings in the resonant frequency band to detect an elevated peak quantity with respect to the baseline spectrum. In some embodiments, comparing 220C zero-crossings may comprise assessing zero-crossing locations to identify one or more new peak locations in the resonant frequency band, i.e., peaks in the signal at frequencies where no peak is present in the baseline spectrum. In some embodiments, comparing 220C zero-crossings may include only one of quantifying the zero crossings and assessing zero-crossing locations.

In some embodiments, calibrating 220A the converted signal comprises dividing the converted signal by a reference spectrum. In some embodiments, the reference spectrum is a "null" spectrum, i.e., an expected spectrum for an ultrasound signal transmitted between the ultrasound transducers without a sample therebetween. For example, the reference spectrum may be an estimated spectrum for an ultrasound signal transmitted through coupling gel and/or other standard components of the system 100 without a sample present. In some embodiments, the reference spectrum may be calculated and/or simulated based on known properties of the coupling gel and/or other components. In another example, the reference spectrum may be determined based on experimental data of an ultrasound signal transmitted between the ultrasound transducers 105/110 without a sample. Accordingly, calibrating 220A the converted signal outputs a spectrum that eliminates spectral features of the ultrasound return signal that are not attributable to the sample.

In some embodiments, differentiating 220B the calibrated signal provides a first derivative of the calibrated signal, whereby each zero-crossing in the first derivative is indicative of peaks in the calibrated signal. Accordingly, peaks in the signal are easily identified on the differentiated signal.

In some embodiments, comparing 220C the zero-crossings within the predetermined resonant frequency bands to a baseline spectrum detects inhomogeneities in the sample. In some embodiments, the baseline spectrum may be an expected spectrum for an ultrasound signal transmitted through a sample lacking inhomogeneities. For example, the baseline spectrum may be an estimated spectrum for obtained from a sample of healthy biological tissue lacking cancerous cells. In some embodiments, the baseline spectrum may be calculated and/or simulated based on known properties of the sample (e.g., the tissue and/or the types of cells therein). In another example, the baseline spectrum may be determined based on experimental data and/or empirical data performed using samples lacking inhomogeneities. For example, the ultrasound signal may be transmitted through healthy tissue samples with known properties and may be analyzed through regression or other mathematical techniques to obtain an expected baseline spectrum for an inhomogeneity-free sample.

In some embodiments, comparing 220C the zero-crossings to a baseline spectrum comprises quantifying the zero-crossings (i.e., counting the number of zero-crossings), which indicates the number of peaks in the resonant frequency band, and comparing the peak quantity to the corresponding peak quantity in the baseline spectrum. As described, a peak quantity that is greater than the baseline value, i.e., an elevated peak quantity, may be indicative of an inhomogeneity in the sample.

In some embodiments, comparing 220C the zero-crossings to the baseline spectrum comprises assessing the zero-crossing locations within the predetermined resonant frequency bands to identify one or more peaks at locations where peaks are not present in the baseline spectrum (i.e., a 'new peak location'). New peak locations indicate a peak in the signal that is not expected in a homogenous sample. Accordingly, the new peak location in the resonant frequency band may be indicative of an inhomogeneity in the sample. By the peak analysis according to any of the techniques described herein, the inhomogeneity may be detected in the sample.

In additional or alternative embodiments, the peak analysis may be performed 220 in additional manners as would be apparent to a person having an ordinary level of skill in the art to detect elevated peak quantities in the resonant frequency bands. In some embodiments, the peak analysis comprises counting peaks in each resonant frequency band to determine a peak quantity and comparing the peak quantities to templates, previous data, empirical data, simulation data, and/or other available data indicative of baseline peak quantities for the resonant frequency bands.

It should be understood that the method 200 as described is particularly advantageous because the use of resonant frequency bands may significantly simplify the analysis of complex samples. This is the case because variations in peak quantity, new peak locations, and/or other deviations in the ultrasound return signal may be indicative of any type of abnormality in the sample rather than the specific type of inhomogeneity of interest. For example, while cancerous cells may be of interest in a tissue sample, other types of abnormalities (e.g., scar tissue) may cause deviations from a baseline spectrum for healthy tissue. Thus, where all instances of elevated peak quantity across the ultrasound return signal are identified, many instances may not correlate with the presence of the inhomogeneity of interest. By the method 200 as described herein, analysis is simplified and sped up by focusing on predetermined resonant frequency bands of interest, wherein elevated peak quantity and/or new peak locations in the resonant frequency bands are known to be indicative of the presence of the inhomogeneity. Therefore, the method 200 herein significantly improves and optimizes the detection of inhomogeneities over conventional methods.

In some embodiments, the system 100 may be utilized as described herein to detect inhomogeneities in a tissue of a patient's anatomy. In some embodiments, the system 100 may be utilized to detect inhomogeneities of a tissue in situ. For example, the system 100 may be applied to the tissue on the patient's body to detect inhomogeneities in the tissue during a surgical procedure, i.e., intra-operatively. In another example, the system 100 may be applied to the tissue on the patient's body post-operatively, during a diagnostic procedure, during a health checkup, and the like as would be apparent to a person having an ordinary level of skill in the art.

In a particular example, the system may be used for assessing breast tissue for the presence of cancer cells after excision of a breast cancer lump. In some embodiments, the sample may be breast cancer margin tissue, i.e., breast tissue at the margin of a cancer site. Typically, the margin tissue must be examined after a cancer lump excision in order to ensure that the tissue is cancer free, i.e., a "negative margin." For example, Ductal carcinoma in situ (DCIS) is an occurrence commonly found in association with invasive breast cancer where the cancer epithelial cells grow abnormally within ductal tubes. DCIS may be difficult to detect in gross pathologic evaluation, especially where imaging is performed pre-operatively and/or where the breast tissue is particularly dense. Where cancer cells remain in the margin tissue (i.e., a "positive margin") after lumpectomy for an invasive breast cancer, re-excision may be required to prevent cancer re-growth and/or metastasis. Accordingly, positive margins may be prevented by detecting cancer cells in the margin tissue using the systems and methods described herein after excision of a breast cancer lump. While conventional methods of detecting cancer cells in tissue margins require a large amount of time and/or must be performed pre-operatively, the procedure described herein may be performed intra-operatively in a short timeframe, e.g., about 1 minute, about 5 minutes, about 10 minutes, about 30 minutes, and/or individual values or ranges therebetween. Accordingly, where a positive margin is detected, additional tissue excision may be performed prior to completion of the surgical procedure in order to remove the cancer cells. Therefore, by the systems and methods described herein, the risks associated with positive tissue margins may be prevented and the need for re-excisions to remove positive tissue margins may be diminished.

While traditional ultrasound methods may often be performed across larger samples (e.g., an entire breast), the use of HFU signals is often limited to thinner samples due to attenuation of the HFU signals. For example, the practicable frequency limit for assessing a given sample may be described as a function of the thickness of the sample, whereby the frequency limit and the thickness of the sample are inversely related. In some embodiments, the sample assessed by the systems and methods described herein may have a thickness of about 100 μm, about 250 μm, about 500 μm, about 1 mm, about 2 mm, about 3 mm, about 4 mm, about 5 mm, about 1 cm, about 2 cm, about 5 cm, or individual values or ranges therebetween. It should be understood that samples of minimal thickness may be assessed by the systems and methods described herein as long as they are capable of being physically placed and contained between the ultrasound transducers 105/110 in a stable manner. Accordingly, while exemplary thicknesses are described herein, the minimum thickness of the sample is only limited by the structure and design of the ultrasound transducers 105/110 and/or the system 100 as a whole.

The devices, systems, and methods as described herein are not intended to be limited in terms of the particular embodiments described, which are intended only as illustrations of various features. Many modifications and variations to the devices, systems, and methods can be made without departing from their spirit and scope, as will be apparent to those skilled in the art.

It should be understood that the system 100 may perform additional filtering and/or processing steps on received ultrasound signals as would be apparent to a person having an ordinary level of skill in the art. In some embodiments, the received signals may be filtered to isolate one or more portions of the received signals. In some embodiments, the received ultrasound signals may be filtered by a high-pass filter or otherwise conditioned in order to improve the signal-to-noise ratio. For example, the high-pass filter may be used to separate the pitch-catch and/or pulse-echo signal from a low frequency standing wave and/or consequences, reflections, or harmonics present in the received ultrasound signal. In some embodiments, the received ultrasound signal may be processed to be digitize, record, and/or convert the signal to a particular form suitable for use in analysis by the system 100 as described herein.

It should also be understood that any number of components of the system 100 may be combined or consolidated without departing from the scope of the invention. In some embodiments, the pulser-receiver 115, the amplifier, the oscilloscope 130, and/or the computing device 135 may be combined or consolidated into a single unit or component. In a particular example, the pulser-receiver 115 and the amplifier may be integrated as a single component which receives the ultrasound signal from the second ultrasound transducer 110 and transmits an amplified ultrasound signal to the oscilloscope 130 and/or the computing device 135.

While the components of the system 100 are described and depicted as having a particular form herein, it should be understood that the components of the system 100 may be provided in a variety of forms to facilitate ease of use and efficiency in assessing samples, especially in the setting of a surgical operating environment before, during, or after a surgical procedure. In some embodiments, the ultrasound transducers 105/110 may be provided as one or more probes, one or more penetrating needles, one or more scalpels (e.g., a microscopic scalpel), a forceps device, a double-needle, one or more surface sensors couplable to the sample, and the like.

The systems and methods disclosed herein are described and depicted as advantageous for detecting breast cancer cells within a breast tissue sample. However, it should be understood that the systems and methods may be used any type of cancer cells in any type of tissue sample as would be apparent to a person having an ordinary level of skill in the art. Furthermore, other types of tissue inhomogeneities may be detected by the systems and methods described herein. For example, the inhomogeneities may be fibrotic cells, fat cells, cells exhibiting another condition or disorder, and/or cells having distinct biomechanical properties from another portion of the sample due to any other cause as would be apparent to a person having an ordinary level of skill in the art.

In some embodiments, the systems and methods described herein may be used on other types of material samples beyond biological tissue. For example, the systems and methods described herein may be applied to synthetic materials, e.g., polymers and other types of generally homogenous materials. In some embodiments, the systems and methods herein may be used to assess a uniformity of the synthetic materials to establish and/or confirm a degree of reliability in manufacturing processes and the like. For example, the systems and methods herein may be used to confirm a general degree of uniformity (i.e., homogeneity) in the synthetic material based on known mechanical properties of the synthetic material. In some embodiments, the systems and methods herein may also be used to detect impurities in the synthetic material in order to determine whether the synthetic material is impurity-free and/or to determine a degree of presence of impurities in the synthetic material. Accordingly, the systems and methods may be advantageous for performing quality assessment of manufactured materials, which is an important and necessary procedure and may be lengthy and/or laborious when performed by conventional means.

In another example, the systems and methods described herein may be applied to natural and/or organic materials, e.g., plant-derived materials and/or other purified or refined substances in the form of solids, waxes, viscous oils and/or liquids, and the like. In some embodiments, the systems and methods herein may be used to assess a purity of the natural and/or organic materials. For example, natural and/or organic materials used for medicinal products, cosmetic products, and/or other consumer products may be tested to ensure a degree of purity in the organic materials. This testing may be required in some instances and may also be used to differentiate the products from similar products of lower quality or purity. Accordingly, the systems and methods herein may be used to detect impurities in the organic materials in order to determine whether the organic material is impurity-free and/or to determine a degree of presence of impurities in the organic material based on known mechanical properties of the organic material. Accordingly, the systems and methods may be advantageous for performing quality assessment of purified and/or refined materials.

Data Processing Systems for Implementing Embodiments Herein

Figure 3:
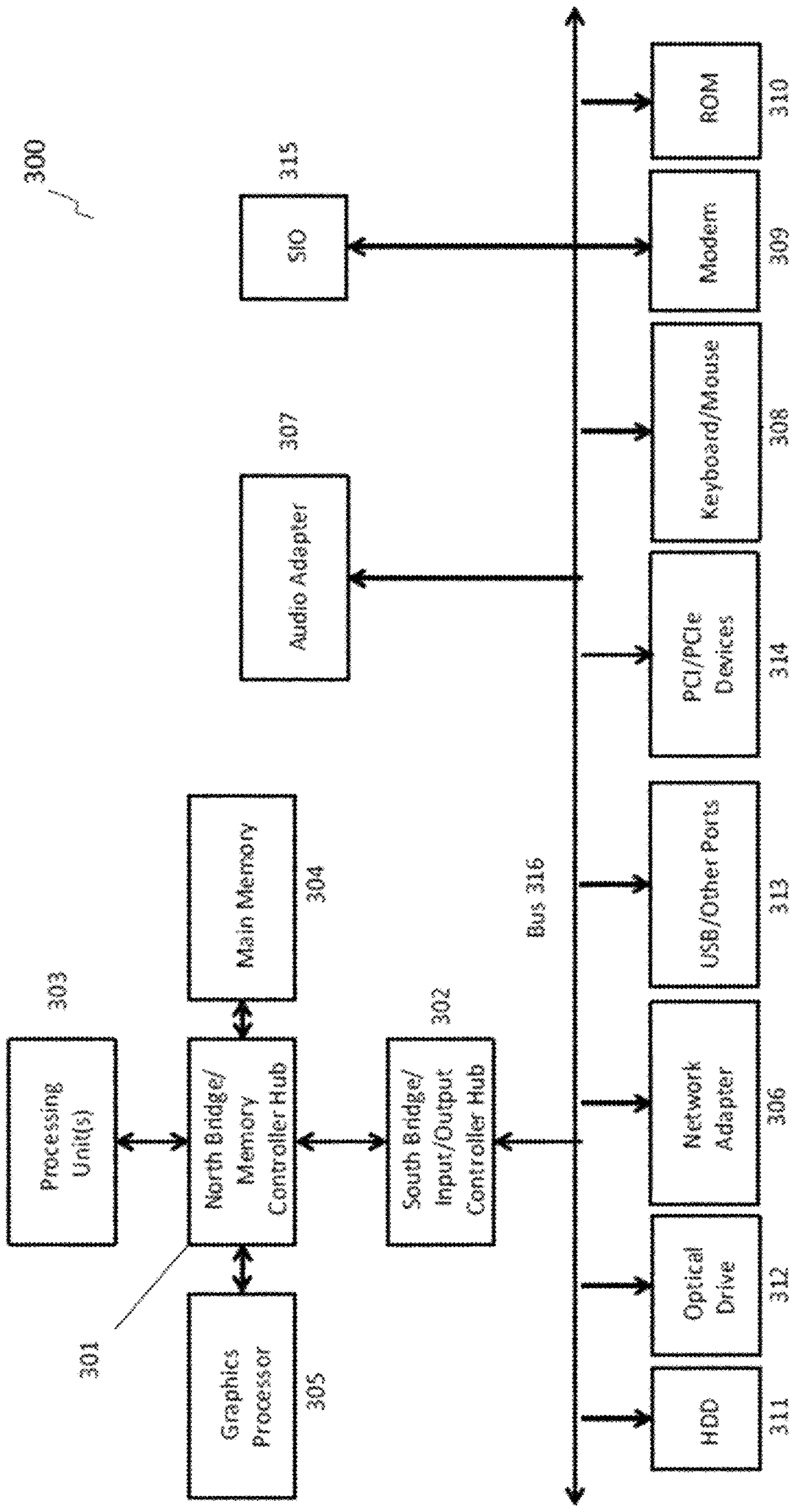
FIG. 3 illustrates a block diagram of an exemplary data processing system in which embodiments are implemented.

FIG. 3 illustrates a block diagram of an exemplary data processing system 300 in which embodiments are implemented. The data processing system 300 is an example of a computer, such as a server or client, in which computer usable code or instructions implementing the process for illustrative embodiments of the present invention are located. In some embodiments, the data processing system 300 may be a server computing device. For example, data processing system 300 can be implemented in a server or another similar computing device as a component of the system 100 as described above. The data processing system 300 can be configured to, for example, transmit and receive signals from the pulser-receiver 115 and other components.

In the depicted example, data processing system 300 can employ a hub architecture including a north bridge and memory controller hub (NB/MCH) 301 and south bridge and input/output (I/O) controller hub (SB/ICH) 302. Processing unit 303, main memory 304, and graphics processor 305 can be connected to the NB/MCH 301. Graphics processor 305 can be connected to the NB/MCH 301 through, for example, an accelerated graphics port (AGP).

In the depicted example, a network adapter 306 connects to the SB/ICH 302. An audio adapter 307, keyboard and mouse adapter 308, modem 309, read only memory (ROM) 310, hard disk drive (HDD) 311, optical drive (e.g., CD or DVD) 312, universal serial bus (USB) ports and other communication ports 313, and PCI/PCIe devices 314 may connect to the SB/ICH 302 through bus system 316. PCI/PCIe devices 314 may include Ethernet adapters, add-in cards, and PC cards for notebook computers. ROM 310 may be, for example, a flash basic input/output system (BIOS). The HDD 311 and optical drive 312 can use an integrated drive electronics (IDE) or serial advanced technology attachment (SATA) interface. A super I/O (SIO) device 315 can be connected to the SB/ICH 302.

An operating system can run on the processing unit 303. The operating system can coordinate and provide control of various components within the data processing system 300. As a client, the operating system can be a commercially available operating system. An object-oriented programming system, such as the Java™ programming system, may run in conjunction with the operating system and provide calls to the operating system from the object-oriented programs or applications executing on the data processing system 300. As a server, the data processing system 300 can be an IBM® eServer™ System® running the Advanced Interactive Executive operating system or the Linux operating system. The data processing system 300 can be a symmetric multiprocessor (SMP) system that can include a plurality of processors in the processing unit 303. Alternatively, a single processor system may be employed.

Instructions for the operating system, the object-oriented programming system, and applications or programs are located on storage devices, such as the HDD 311, and are loaded into the main memory 304 for execution by the processing unit 303. The processes for embodiments described herein can be performed by the processing unit 303 using computer usable program code, which can be located in a memory such as, for example, main memory 304, ROM 310, or in one or more peripheral devices.

A bus system 316 can be comprised of one or more busses. The bus system 316 can be implemented using any type of communication fabric or architecture that can provide for a transfer of data between different components or devices attached to the fabric or architecture. A communication unit such as the modem 309 or the network adapter 306 can include one or more devices that can be used to transmit and receive data.

Those of ordinary skill in the art will appreciate that the hardware depicted in FIG. 3 may vary depending on the implementation. Other internal hardware or peripheral devices, such as flash memory, equivalent non-volatile memory, or optical disk drives may be used in addition to or in place of the hardware depicted. Moreover, the data processing system 300 can take the form of any of a number of different data processing systems, including but not limited to, client computing devices, server computing devices, tablet computers, laptop computers, telephone or other communication devices, personal digital assistants, and the like. Essentially, data processing system 300 can be any known or later developed data processing system without architectural limitation.

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples:

EXAMPLES

Example 1: Frequency Response of Single Cell Visco-Elastic System: Theoretical Analysis Background. The goal of this analysis is to calculate the natural frequencies of cancer epithelial cells and healthy cells. These calculations will provide a benchmark for our experimental and simulation analysis. This will be used to determine the range of frequencies that may be needed to resonate healthy and cancerous epithelial cells in breast.

Figure 4:
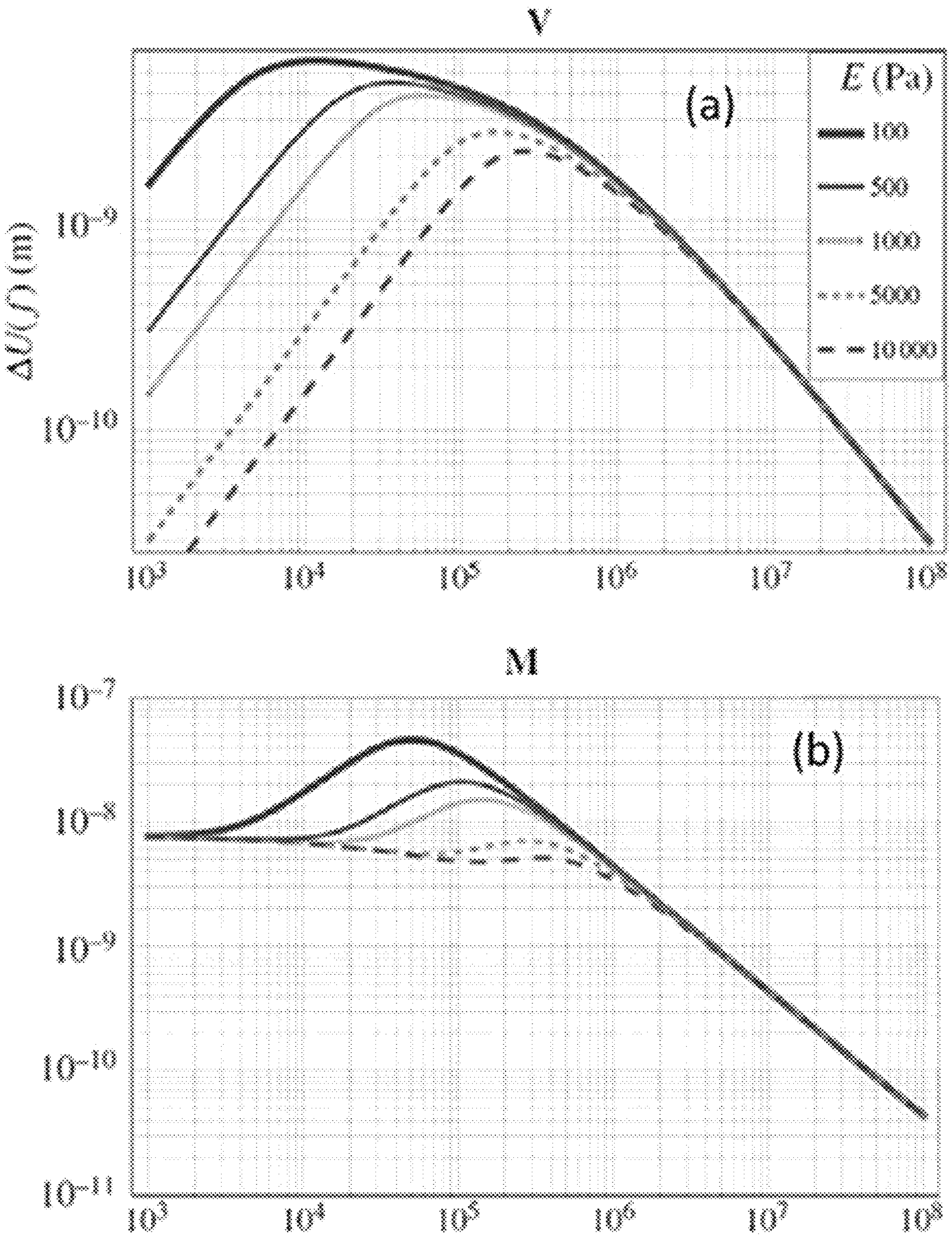
FIG. 4 depicts sensitivity analyses for the frequency response of the cyclic displacement amplitude of a spherical object with respect to its surroundings in accordance with an embodiment.

Methods. Single cell dynamic within a visco-elastic media can be modeled using Voigt and Maxwell viscoelastic constructs. Since nucleus is much stiffer than cytoplasm and occupies a large portion of the medium, it is reasonable to assume nucleus vibration is the dominant factor. The system consists of a nucleus embedded in viscous fluid. The motion of the nucleus can be described using Voigt and Maxwell viscoelastic constructs. FIG. 4 depicts an illustrative theoretical model of mechanical oscillation of the cell using an ultrasound source and a theoretical representation of forces acting on the cell in accordance with an embodiment. In the Voigt model, the elastic and viscous elements are acting parallel on the nucleus. Therefore, the total force is the summation of these two forces, as described by $F_R=F_\mu+F_E$ where $F_R$ is the response force, $F_\mu$ is the viscous force, and $F_E$ is the elastic shear response. However, in the Maxwell model, the forces are in series and therefore they are equal, as described by $F_R=F_\mu=F_E$, where $F_R$ is the response force, $F_\mu$ is the viscous force, and $F_E$ is the elastic shear response. There are other models that will be examined, in order to find the most appropriate model for the particular cancer cell of interest.

Preliminary Results and Discussion. Preliminary analysis by means of theoretical arguments has demonstrated that single cells, modeled through different elementary viscoelastic systems, exhibit frequencies associated with oscillation magnitude peaks. FIG. 4 depicts sensitivity analyses for the frequency response of the cyclic displacement amplitude of a spherical object with respect to its surroundings in accordance with an embodiment. As shown in FIG. 4, the vibration amplitude calculated using Voigt and Maxwell models show a maximum amplitude within the examined range of frequencies. This confirms that a mechanical resonance-like phenomenon can be induced by ultrasound.

However, there are large variabilities associated with available data for the cell and nuclei shape and sizes and mechanical stiffness. Additionally, further studies on the overall cell viscosity demonstrated that rheological properties may span over five orders of magnitude, which could potentially change the overall response significantly. For example, while the viscosity of aqueous cytoplasm was found to be similar to that of water in fibroblasts, and slightly higher in smooth muscle cells, viscosity of blood granulocytes was instead estimated to be substantially higher. Variation of rheological properties makes the calculation very sensitive to the input data.

Additionally, there are certain assumptions associated with the theoretical models such as number of degrees of freedom, the size comparison between the cell and the ultrasound wavelength and regular shape of the nucleus. For cancer cells, any of these characteristics can randomly change. For example, the shape of the cell and size and shape of nucleus are known to change because of cancer. Although theoretical models are excellent in providing estimates and benchmarks for our analysis, these models are limited in obtaining results in more complicated situations such as a cluster of cells. Accordingly, a multi-physics finite element model is needed to evaluate the response of the system accurately.

The Voigt model can be described by Equation 1:

$$\text{VOIGT: } |\Delta u|_{s=i\omega} = \left| \frac{\frac{4}{3}\pi\gamma\zeta\rho_m R^3 s V_m}{C_{0E} + (C_{1\mu} + C_{1E})s + \left((C_{2\mu} + C_{2E}) + \left(\frac{4}{3}\right)\pi\rho_{0b}R^3\right)s^2} \right|_{s=i\omega} \quad (1)$$

and the Maxwell model can be described by Equation 2:

$$\text{Maxwell: } |\Delta u|_{s=i\omega} = \left| \frac{\frac{4}{3}\pi\gamma\zeta\rho_{0b} R^3 s V_m}{1 + \left(\frac{4}{3}\right)\pi\rho_{0b}R^3 s^2 \left(\frac{1}{(C_{1\mu}s + C_{2\mu}s^2)}\right) + \left(\frac{1}{(C_{0E} + C_{1E}s + C_{0E}s^2)}\right)} \right|_{s=i\omega} \quad (2)$$

where $\rho_m$ is the density of the medium, $\rho_{0b}$ is the nucleus density, $\Delta u$ is the displacement amplitude, $\omega_0$ the angular frequency of the oscillation, R is the radios of nucleus, s is the Laplace variable, G is the shear modulus of the medium, and where $C_{0E}$, $C_{1E}$, $C_{2E}$, $C_1\mu$, and $C_2\mu$ are defined by Equations 3-7, respectively:

$$C_{0E} = 6\pi GR \quad (3)$$

$$C_{1E} = 6\pi R^2\sqrt{G\rho_m} \quad (4)$$

$$C_{2E} = \frac{2}{3p}\pi R^3\rho_m \quad (5)$$

$$C_{1\mu} = 6\pi R\mu\left(1 + \sqrt{\frac{\omega R^2}{2v}}\right) \quad (6)$$

$$C_{2\mu} = \frac{2}{3P}\pi R^3\rho_m\left(1 + \frac{9P}{2}\sqrt{\frac{2v}{\omega R^2}}\right) \quad (7)$$

Example 2: Computational Modeling of Single Cell Response and Cell Clusters Response Methods. Theoretical analyses are limited to single cell response. Additionally, multi-cell response becomes significantly more challenging to be solved in analytical manner. Therefore, a finite element simulation is developed to characterize a single cell behavior as well as a cluster of cancer cells in response to exposure to ultrasound waves within a certain range of frequencies. The goal of this analysis is to examine the possibility of resonating the cells and demonstrating the response in the frequency spectrum. Based on our hypothesis, the resonation should provoke a peak and multiple peaks around the resonance frequency in the frequency response.

In this study, finite element high-frequency ultrasound analysis is conducted to evaluate multiple forward acoustic scattering to understand how cancerous cells or clusters respond to the ultrasound wave. Important factors from the histological grading such as nuclear pleomorphism and malignant cell density will be modeled through either increasing the number of cancerous cells or changing the visco-elastic properties of cancerous cells according to findings in literature.

Figure 5:
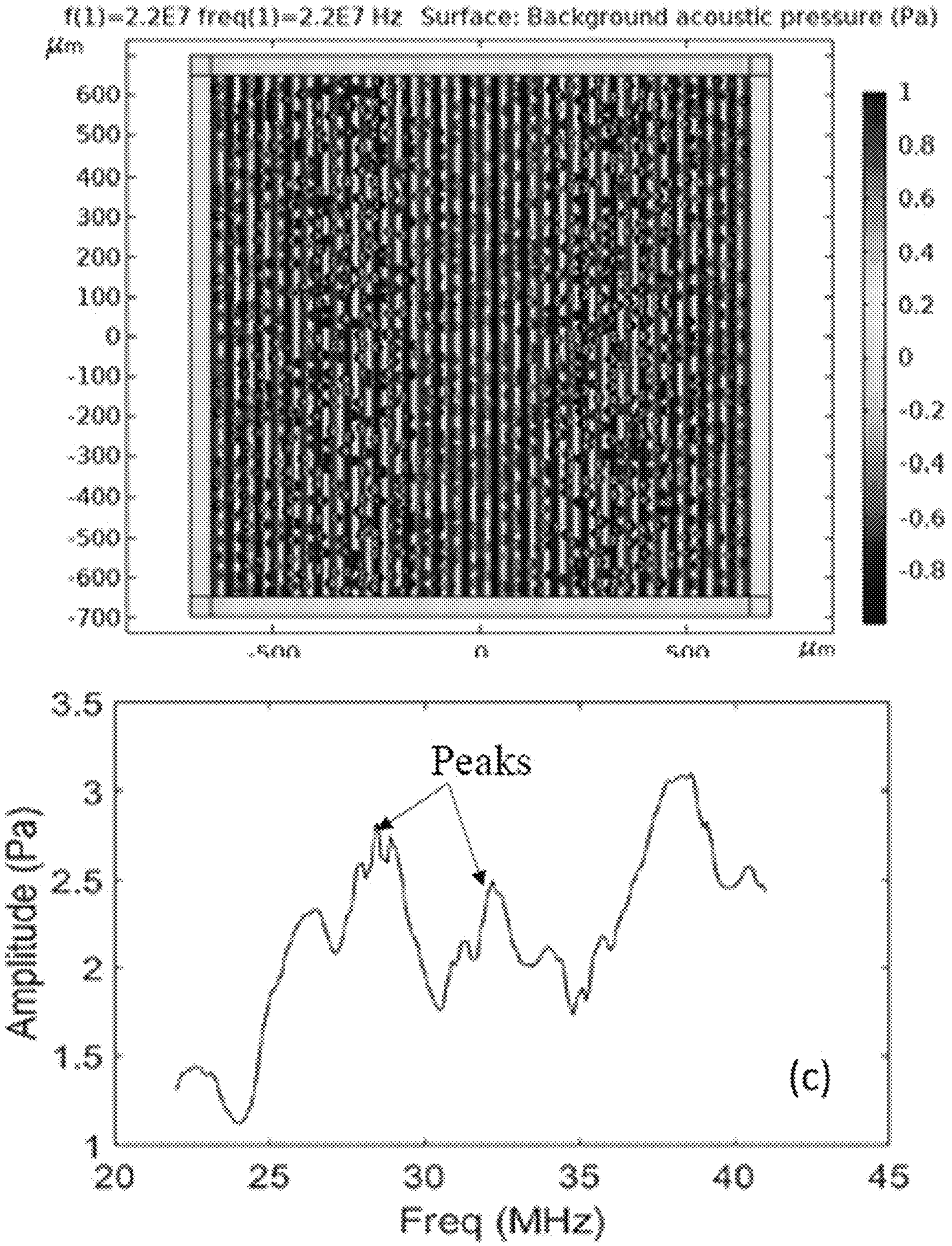
FIG. 5 depicts a finite element simulation of clusters of healthy and cancerous cells in accordance with an embodiment.
Figure 6A:
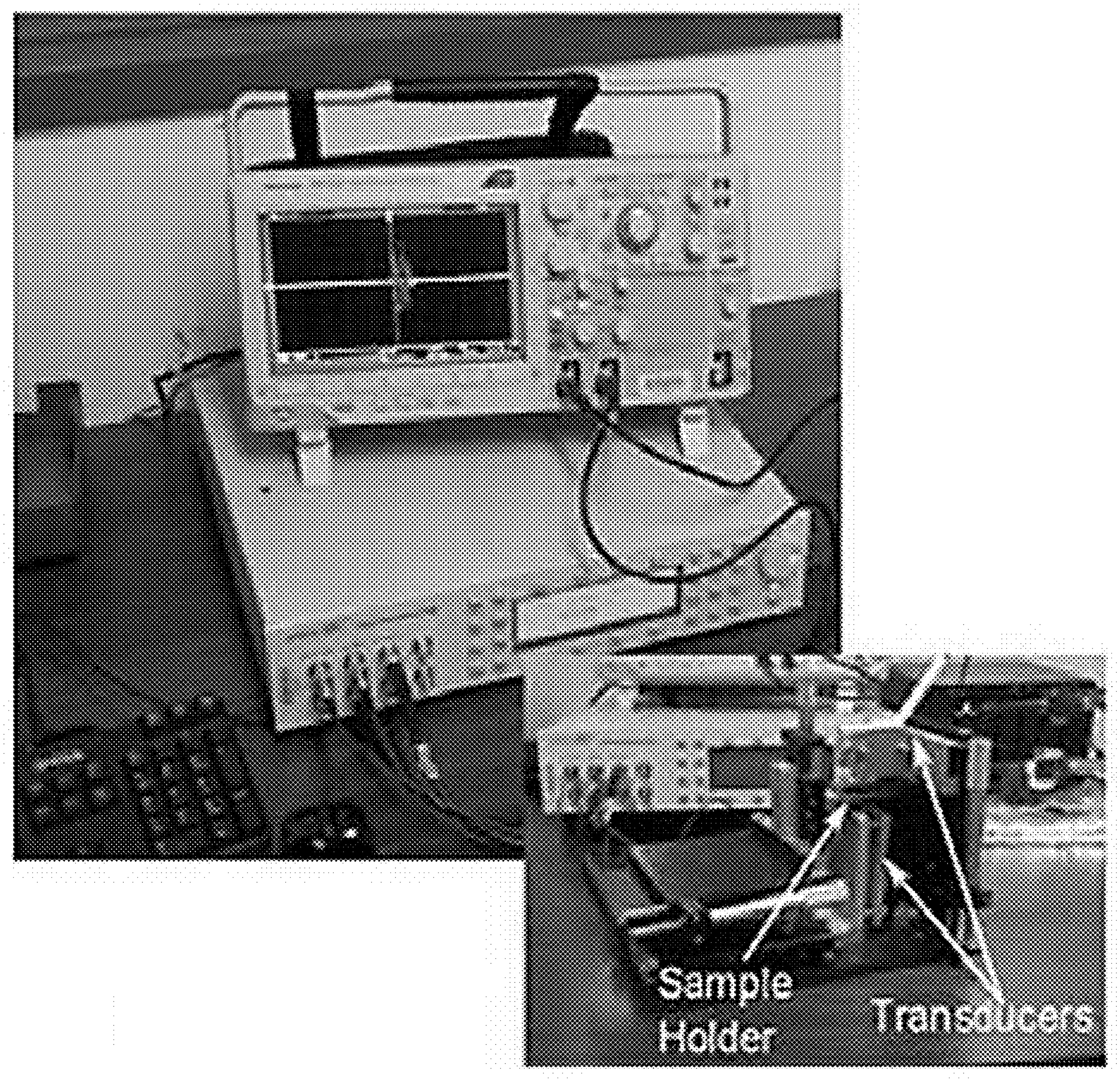
FIGS. 6A-6D depict an experimental setup and related results for assessing biological response of healthy and cancerous cells in accordance with an embodiment.
Figure 6B:
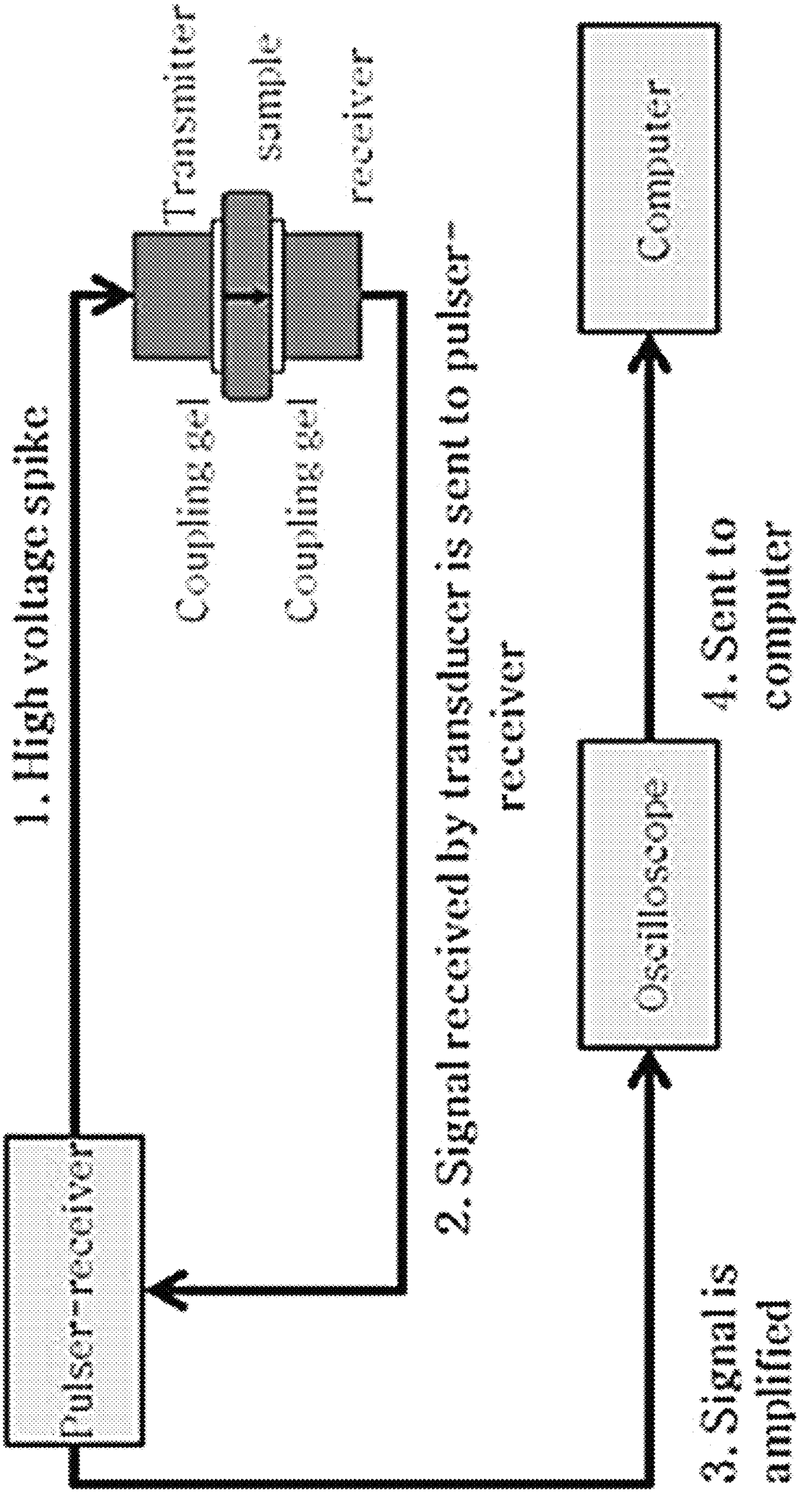
Figure 6C:
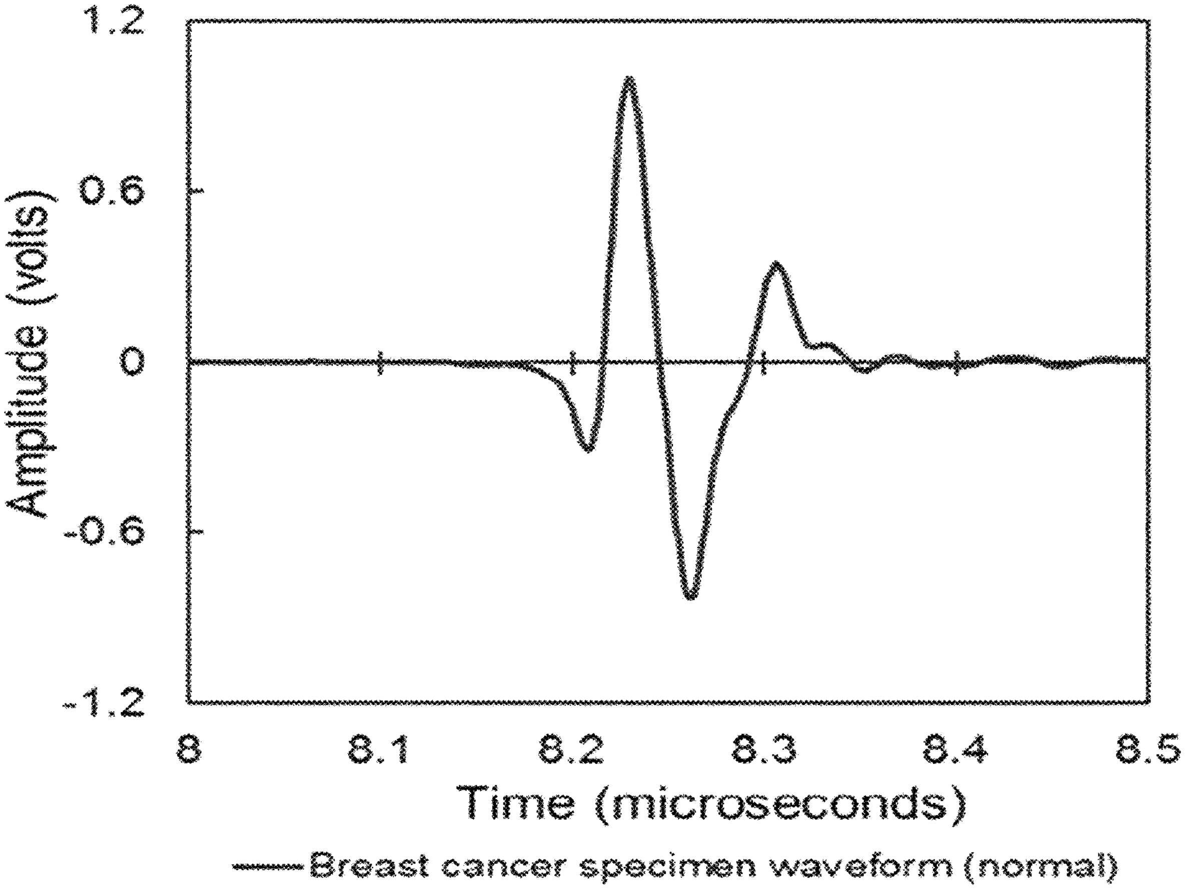
Figure 6D:
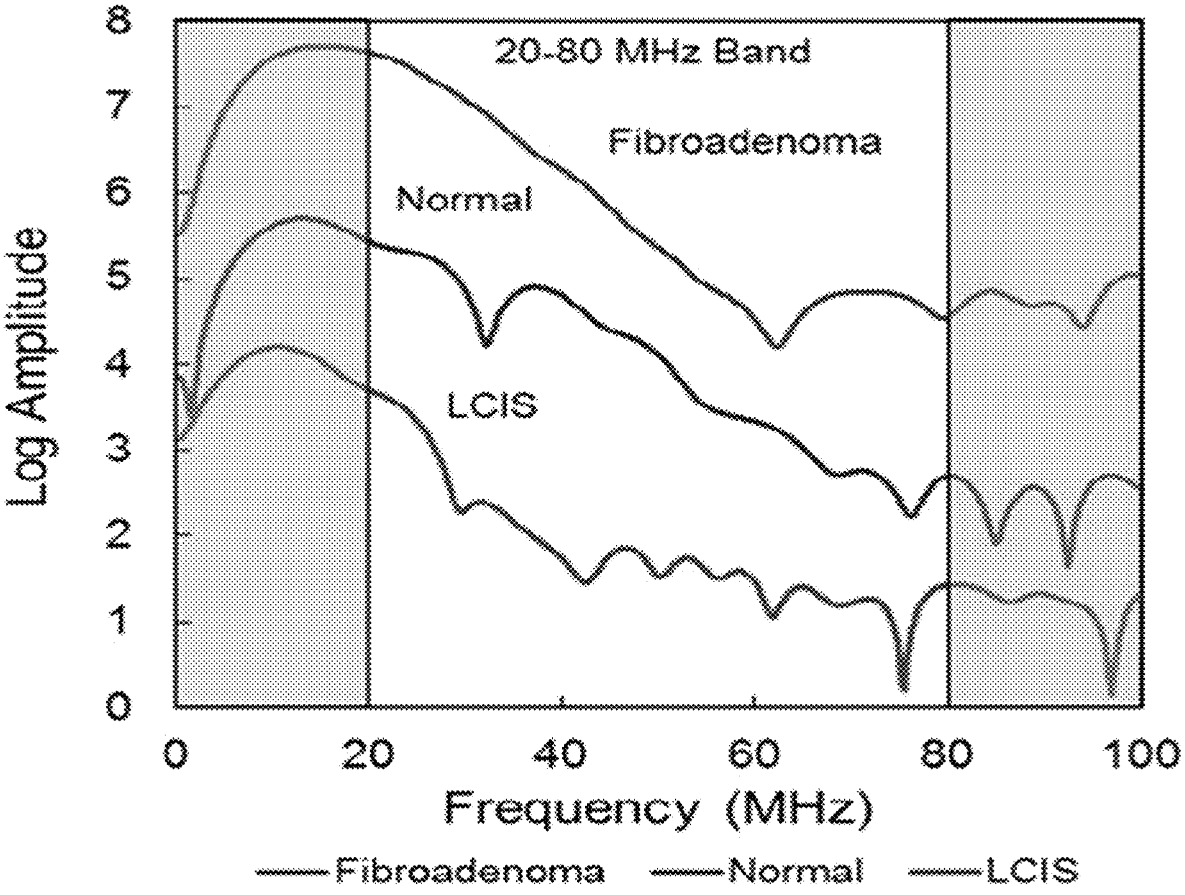
Figure 7A:
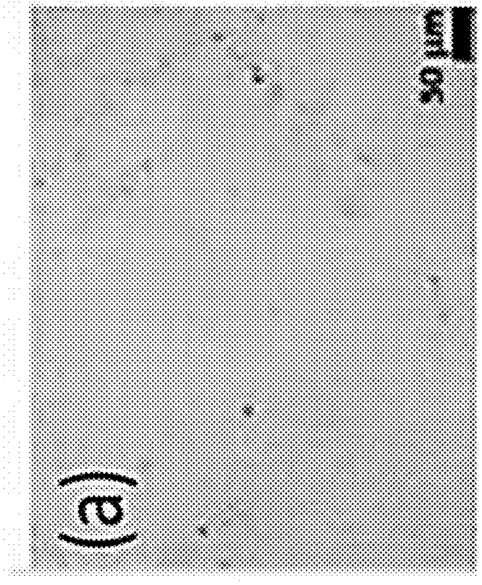
FIGS. 7A-7F depict experimental and computational models of forward scattering of high frequency ultrasound in tissue phantoms containing inhomogeneities of controlled size and distribution density in accordance with an embodiment.
Figure 7B:
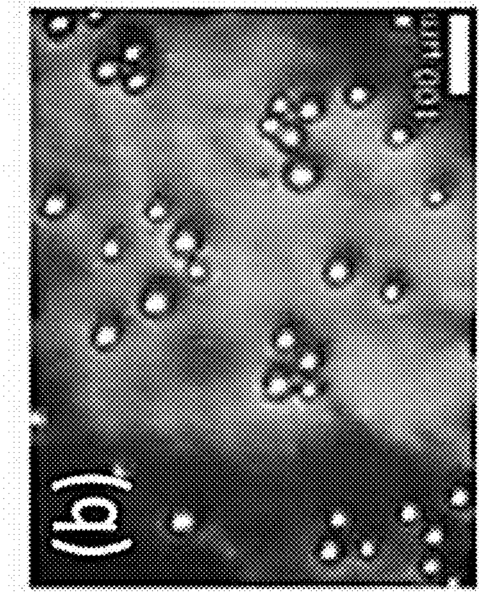
Figure 7C:
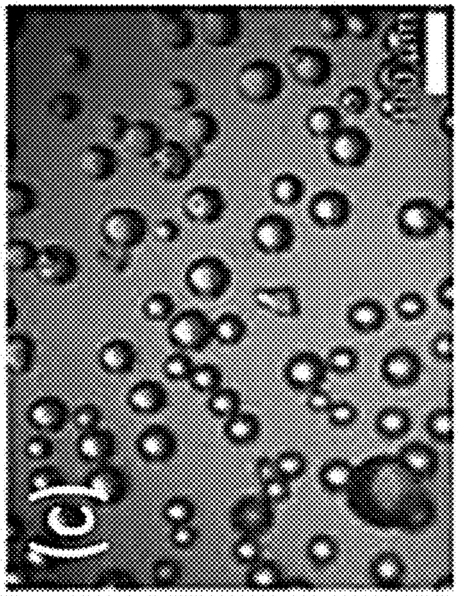
Figure 7D:
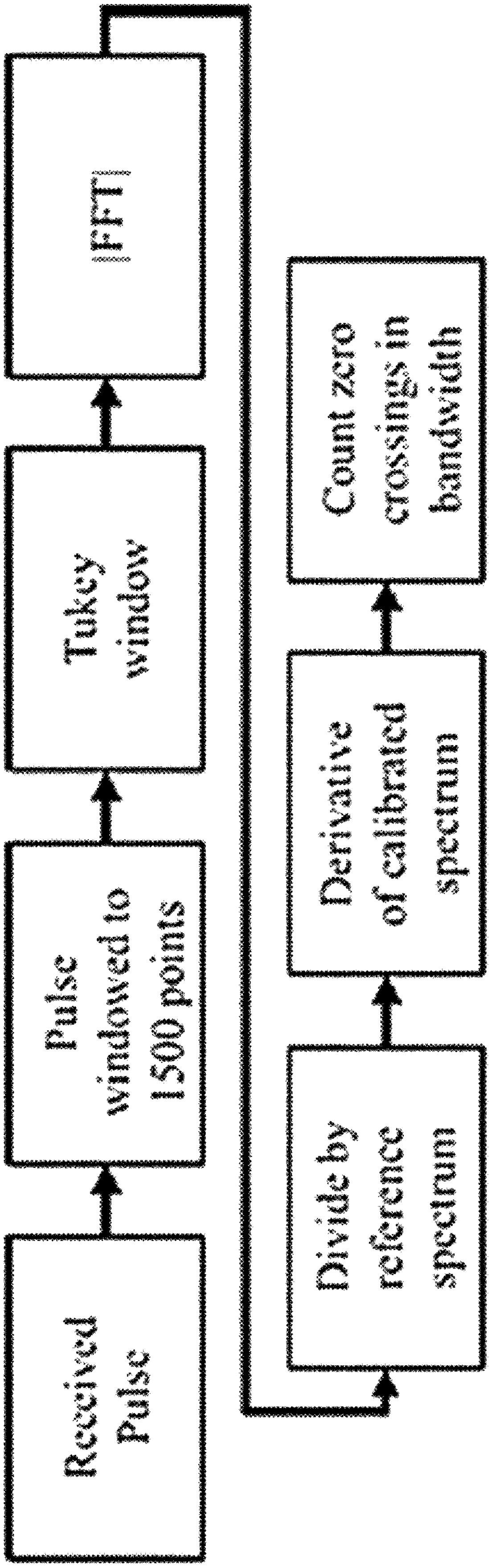
Figure 7E:
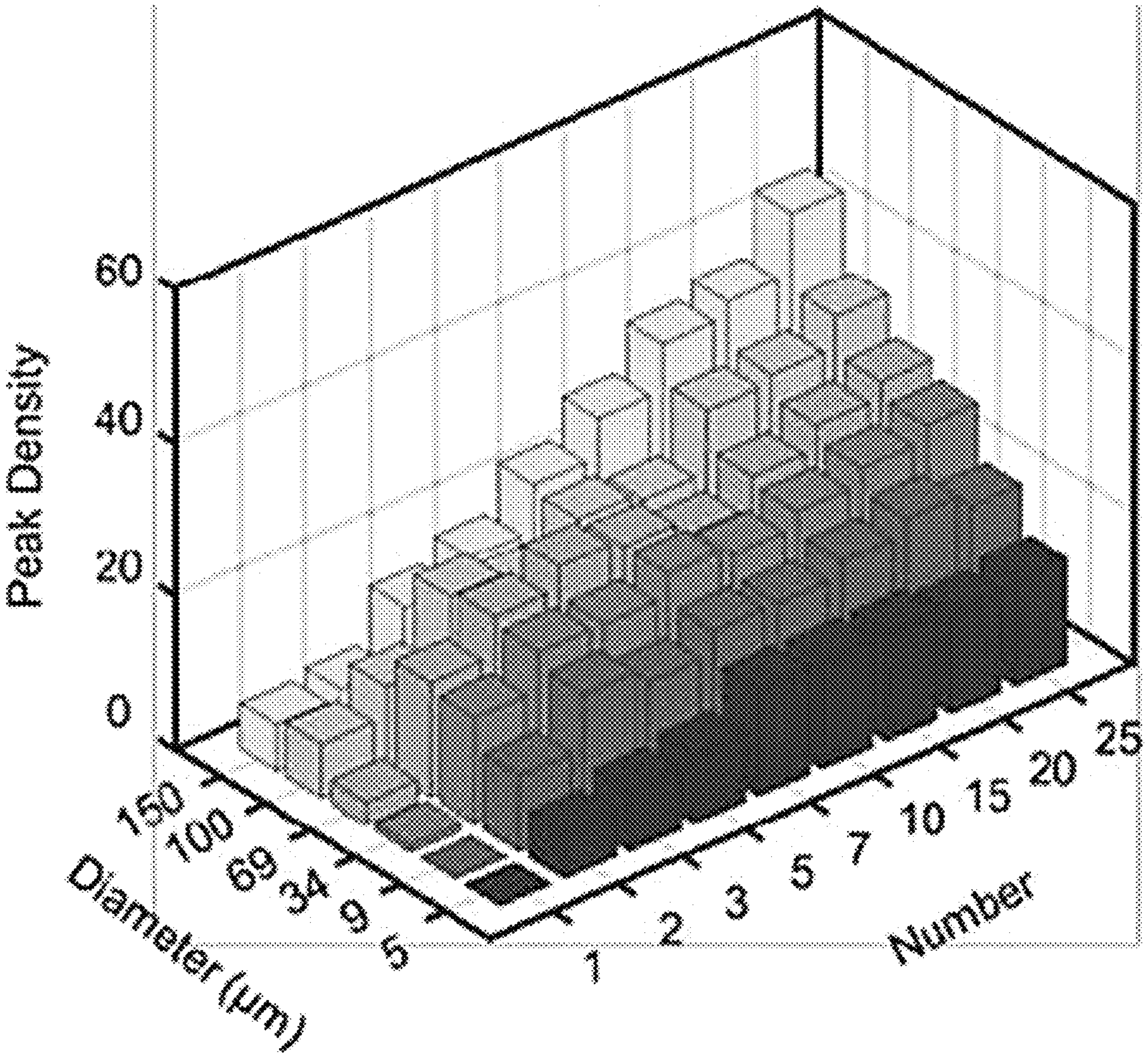
Figure 7F:
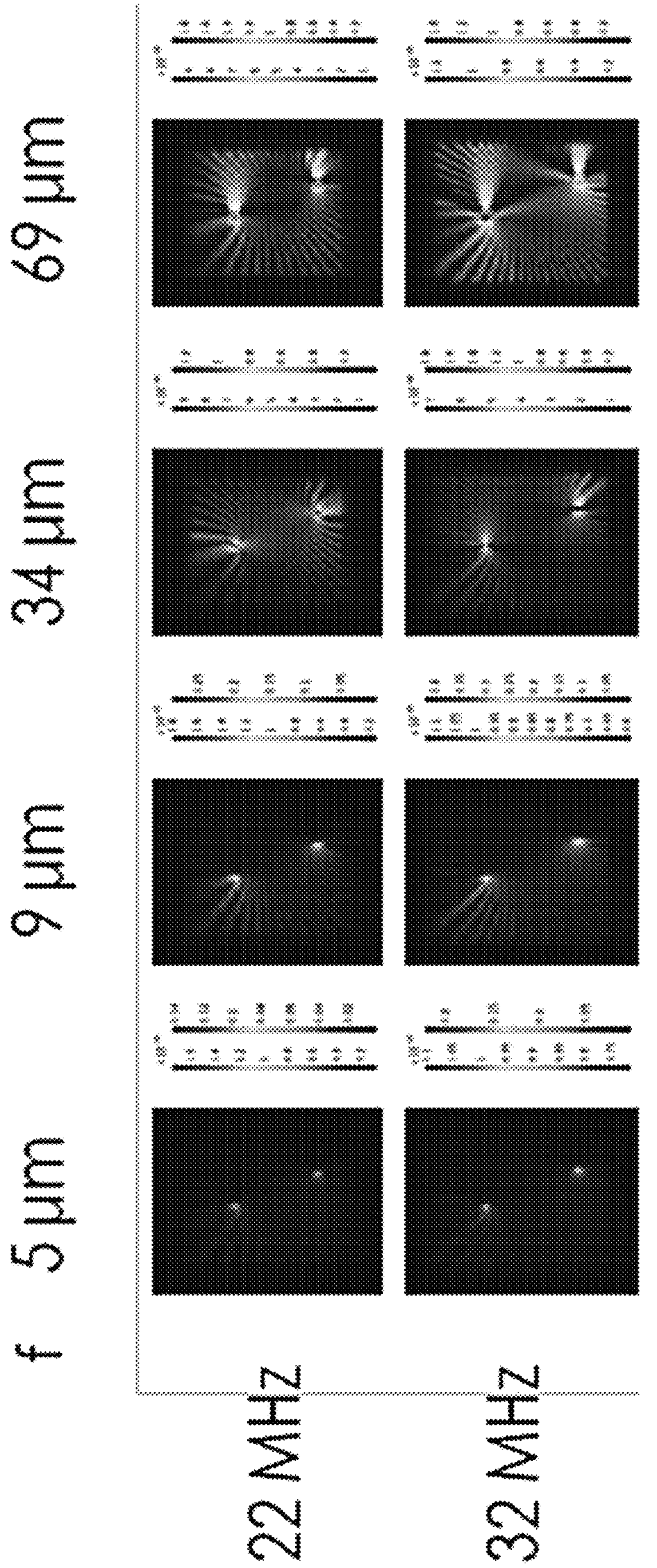

Preliminary Results and Discussion. FIG. 5 depicts a finite element simulation of clusters of healthy and cancerous cells in accordance with an embodiment. This preliminary analysis was conducted in a liquid medium with nucleus represented as solid for cancerous and healthy cells. The governing equations for wave propagation are defined by Helmholtz equations described in Equations 8 and 9:

$$\nabla \cdot \left(-\frac{1}{\rho_c}(\nabla p_t - q_d)\right) - \frac{k_{eq}^2}{\rho_c} p_t = Q_m \tag{8}$$

$$k_{eq}^2 = \left(\frac{2\pi f}{c_c} - i\ln 10\frac{\alpha}{20}\right)^2 - k_z^2 = k^2 - k_z^2 \tag{9}$$

where $c_c$ is the speed of sound, α is the attenuation coefficient, f is the frequency, $k_{eq}$ is the equivalent wave number, $k_z$ is the out of plane wave number, $Q_m$ is the monopole source, $q_d$ is the dipole source, $\rho_c$ is the medium density, $p_t$ is the total pressure, $p_b$ is the background pressure field, and $p_s$ is the scattered pressure field. The models will be modified to be more realistic representing Voigt-Maxwell visco-elastic behavior in all three-medium including the nucleus, cytoplasm and extracellular matrix. Different response parameters, such as the peak quantity, the frequencies at which these peaks are observed in the response and mean peak to valley distances are obtained from the simulation. Furthermore, the spectral pattern will be analyzed to find out significant features of the spectrum against various malignant features.

Example 3: Frequency Response Analysis of Cancer Cells and Clusters

Methods. Analysis will be expanded by conducting similar experiments on tissues containing cancer cells or cancer cell clusters. The goal is to experimentally verify mechanobiological response of cancer cells to HFU. Experiments will have the elements that simulation is missing such as biological response which cannot easily be modeled in simulation. To analyze single cell and cluster of cells response to HFU, an apparatus and test set up is used. FIGS. 6A-6D depict an experimental setup for assessing biological response of healthy and cancerous cells in accordance with an embodiment. An HFU wave in frequency bandwidths that are expected to resonate or create high scattering in cancer cells is sent through the material and received from the other side (i.e., pitch-catch method). The thickness of samples is selected accordingly to avoid attenuation and diminishing of the signal. Two single element transducers are used for sending and receiving signals. The receiving signal is then analyzed by converting the signal from time domain to a frequency domain using Fast Fourier Transform (FFT) technique.

This method is a new approach in characterizing the frequency response based on the hypothesis that theoretically the peak quantity (number of peaks) observed in the receiving signal around resonance frequency of the cancer cells should be significant. The main concept in the present approach is to use algorithms to determine the peaks that occur at certain frequencies in the resulting signal.

As shown in FIGS. 6A-6D, the FFT signal shows different characteristics for healthy tissues versus tissues with different levels of cancer growth. The number of peaks and valleys observed in the FFT spectrum is indicative of the microstructure and the number of scatterers that exist in the microstructure. The high frequency provides sensitivity to the smaller elements in microstructure and provides a better accuracy.

Currently, the ultrasound waveforms sent through the material are digitized at 1.25 GS/s using a digital oscilloscope (DPO 3052, Tektronix, Inc., Beaverton, OR, USA) and to reduce noise, the first 512 pulses are averaged. Signal generation and acquisition are automated with LabView (National Instruments). These signals are then analyzed using MATLAB algorithm to evaluate the resulting power spectrum density signal and determine the peaks and valleys and the range of important frequencies. Given that each signal is sent/received and analyzed in a very small fraction of a second, it only takes a few seconds to conduct each test.

Experiments will be conducted in three different scenarios: (1) small number of breast cancer epithelial cells in tissue culture, (2) a cluster of the cancer cell lining in tissue culture, (3) actual experiments on (DCIS) cases. This is to distinguish the scales at which the hypothesis may stand true.

Anticipated Results. It is anticipated that the identifiable biomechanical response of cancer cells will be unique and distinguishable from healthy cells in each of the three assessed scenarios such that cancer cells may be distinguished from healthy cells based on the described protocol and experimental setup.

Example 4: Experimental Analysis Using Tissue Phantoms

Methods. Experimental analysis has been performed using tissue phantoms and glass microbeads as inhomogeneities (e.g. cancer cells) as well as simulation and modeling of the same.

Results and Discussion. FIGS. 7A-7F depicts experimental and computational models of forward scattering of high frequency ultrasound in tissue phantoms containing inhomogeneities of controlled size and distribution density in accordance with an embodiment. As shown in the initial analysis, peak density is sensitive to the number of scatters and the size of thereof. This is confirmed through both experiments and 2D computational modeling of forward scattering of HFU in tissue phantoms. FIG. 8A is a photograph of a phantom with 9 μm microspheres with 1 $mm^{-3}$ density. FIG. 8B is a photograph of a phantom with 34 μm microspheres with 25 $mm^{-3}$ density. FIG. 8C is a photograph of a phantom with 69 μm microspheres with 50 $mm^{-3}$ density. FIG. 8D is a flowchart of the signal processing steps utilized to assess the peak density. Simulation of wave scattering in several cases made up of two scatterers with different diameters in different in frequencies of 22 and 32 MHz are also presented in FIG. 8F. As shown, when the number of scatterers and their size increases, the peak density increases as well.

Example 5: Histology-Based Modeling and Simulation

Methods. Histology-based modeling and simulation was performed where cancer cells were modeled within healthy tissue cells. In the histology-based modeling, finite element high-frequency ultrasound analysis was conducted to evaluate multiple forward acoustic scattering to detect different histological features of cancerous tissue. In a systematic design of experiment (DoE) conducted, two important factors from the histological grading were considered for the tissue modeling which was nuclear pleomorphism (increase in the size of the nucleus) and malignant cell density. The DOE also included two different cellular shapes-circular for initial approximation and elliptical for a close approximation.

Figure 8:
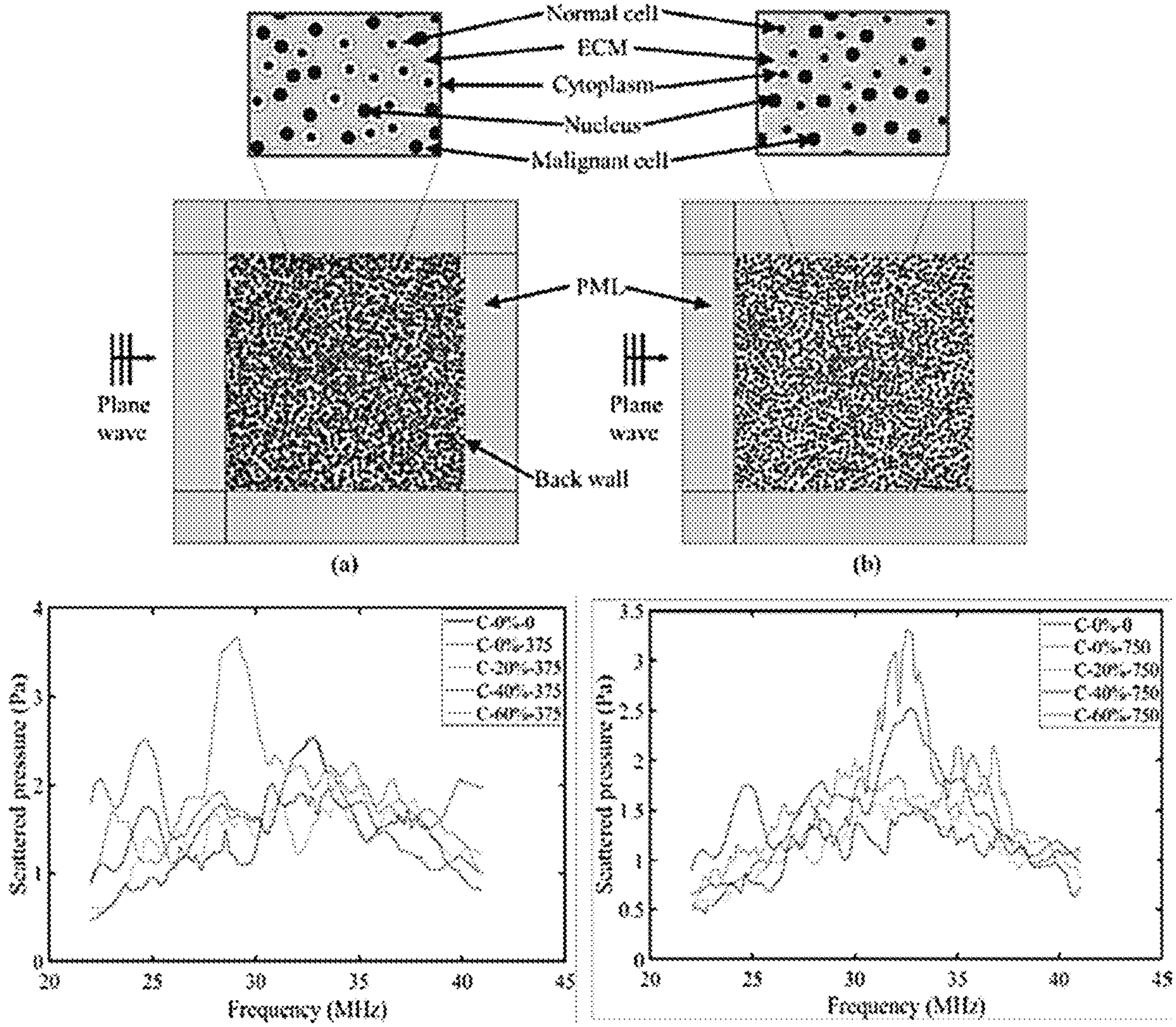
FIG. 8 depicts histology-based modeling of forward scattering in frequency bandwidth of 22-41 MHz for different experimental cases in accordance with an embodiment.

Results. FIG. 8 depicts histology-based modeling of forward scattering in frequency bandwidth of 22-41 MHz for different experimental cases in accordance with an embodiment. As shown, two examples within the 22 to 41 MHz frequency range were used in this study to keep similarity with the previous research. Different response parameters were evaluated in this study. One of the response parameters was spectral peak density that was found very responsive against microstructural changes. The average magnitude difference between all the adjacent peak and valleys were analyzed which was called Mean Peak to Valley Distance (MPVD). Furthermore, the spectral pattern was analyzed to find out significant features of the spectrum against various malignant features. It was observed that with cellular structures tending towards the cancerous level, peak density increased and MPVD value decreased. Also, the cancer cell density contributed more to the multiple scattering than the pleomorphism.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Instead, this application is intended to cover any variations, uses, or adaptations of the present teachings and use its general principles. Further, this application is intended to cover such departures from the present disclosure as come within known or customary practice in the art to which these teachings pertain. Many modifications and variations can be made to the particular embodiments described without departing from the spirit and scope of the present disclosure as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for detecting one or more inhomogeneities in a material sample, wherein the one or more inhomogeneities have one or more predetermined resonant frequencies, the system comprising:

a pulser-receiver configured to generate one or more electrical pulses;

a first ultrasound transducer configured to be arranged on a first side of the material sample, wherein the first ultrasound transducer is configured to generate one or more high frequency ultrasound (HFU) signals in response to receiving the one or more electrical pulses, wherein the one or more HFU signals propagate through the material sample and undergo scattering therein;

a second ultrasound transducer configured to be arranged on a second side of the material sample opposite the first side, wherein the second ultrasound transducer is configured to receive the one or more scattered HFU signals from the material sample and transmit one or more electronic signals indicative of the one or more scattered HFU signals to the pulser-receiver;

a processor; and a non-transitory, computer-readable medium storing instructions that, when executed, cause the processor to:

receive the one or more electronic signals from the pulser-receiver, generate a windowed signal based on the one or more electronic signals by applying a window function, convert the windowed signal to frequency domain via fast Fourier transform, determine, for the converted signal, a peak quantity within one or more resonant frequency bands associated with the one or more predetermined resonant frequencies, wherein the one or more resonant frequency bands comprise a resonant frequency band for each of the one or more predetermined resonant frequencies, wherein each frequency band comprises a frequency bandwidth including the predetermined resonant frequency, and compare the peak quantity to a baseline value, wherein a peak quantity greater than the baseline value is indicative of a presence of the one or more inhomogeneities in the material sample.

2. The system of claim 1, wherein the first ultrasound transducer is in electrical communication with the pulser-receiver via a first ultrasound transmission line and the second ultrasound transducer is in electrical communication with the pulser-receiver via a second ultrasound transmission line.

3. The system of claim 1, wherein, in response to receiving the one or more electrical pulses, the first ultrasound transducer is configured to oscillate at a frequency bandwidth between 0.5 MHz and 100 MHz, thereby generating the HFU signal.

4. The system of claim 1, further comprising an oscilloscope in electrical communication with the pulser-receiver, wherein the oscilloscope is configured to receive the electronic signal from pulser-receive and digitize the electronic signal, wherein instructions that cause the processor to receive the electronic signal from the pulser-receiver comprise instructions that, when executed, cause the processor to receive the digitized electronic signal from the pulser-receiver via the oscilloscope.

5. The system of claim 1, wherein the instructions that cause the processor to window the electronic signal comprise instructions that, when executed, cause the processor to:

isolate an interval of the electronic signal; and multiply the interval of the electronic signal by the window function, thereby generating a tapered waveform of the interval.

6. The system of claim 1, wherein the instructions that cause the processor to determine a peak quantity of the converted signal comprise instructions that, when executed, cause the processor to:

calibrate the converted signal;

differentiate the calibrated signal; and count zero-crossings in the differentiated signal within the one or more resonant frequency bands to determine the peak quantity.

7. The system of claim 6, wherein the instructions that cause the processor to calibrate the converted signal comprise instructions that, when executed, cause the processor to divide the converted signal by a reference spectrum.

8. The system of claim 1, wherein the baseline value is determined based on one or more of historical data, empirical data, and a simulation based on one or more known characteristics of the material sample.

9. The system of claim 1, wherein the one or more predetermined resonant frequencies are predetermined based on one or more of historical data, empirical data, and a simulation based on one or more known characteristics of the one or more inhomogeneities.

10. The system of claim 1, wherein the HFU signal comprises the one or more predetermined resonant frequencies.

11. The system of claim 1, wherein the first ultrasound transducer and the second ultrasound transducer are arranged in a pitch-catch arrangement.

12. The system of claim 1, wherein the material sample comprises a biological tissue sample and the one or more inhomogeneities comprise one or more cells exhibiting a condition.

13. The system of claim 1, wherein the material sample comprises a breast tissue sample and the one or more inhomogeneities comprise one or more breast cancer cells.

14. The system of claim 1, wherein:

the one or more electrical pulses comprise a plurality of electrical pulses;

the one or more HFU signals comprise a plurality of HFU signals;

the one or more scattered HFU signals comprise a plurality of scattered HFU signals; and the one or more electronic signals comprise a plurality of electrical signals.

15. The system of claim 14, wherein the instructions, when executed, further cause the processor to average the plurality of electronic signals to obtain an averaged signal, wherein the windowed signal is based on the averaged signal.

16. The system of claim 1, wherein the instructions, when executed, further cause the processor to control the pulser-receiver to generate the one or more electrical pulses.

17. The system of claim 1, further comprising an amplifier in electrical communication with the pulser-receiver and configured to amplify the one or more electronic signals, wherein the one or more electronic signals received by the processor from the pulser-receiver comprise amplified electronic signals received from the pulser-receiver via the amplifier.

18. A system for detecting one or more inhomogeneities in a material sample, wherein the one or more inhomogeneities have one or more predetermined resonant frequencies, the system comprising:

a pulser-receiver configured to generate one or more electrical pulses;

a first ultrasound transducer configured to be arranged on a first side of the material sample, wherein the first ultrasound transducer is configured to generate one or more high frequency ultrasound (HFU) signals in response to receiving the one or more electrical pulses, wherein the one or more HFU signals propagate through the material sample and undergo scattering therein;

a second ultrasound transducer configured to be arranged on a second side of the material sample opposite the first side, wherein the second ultrasound transducer is configured to receive the one or more scattered HFU signals from the material sample and transmit one or more electronic signals indicative of the one or more scattered HFU signals to the pulser-receiver;

a processor; and a non-transitory, computer-readable medium storing instructions that, when executed, cause the processor to:

receive the one or more electronic signals from the pulser-receiver, generate a windowed signal based on the one or more electronic signals by applying a window function, convert the windowed signal to frequency domain via fast Fourier transform, determine, for the converted signal, one or more peak frequencies within one or more resonant frequency bands associated with the one or more predetermined resonant frequencies, wherein the one or more resonant frequency bands comprise a resonant frequency band for each of the one or more predetermined resonant frequencies, wherein each frequency band comprises a frequency bandwidth including the predetermined resonant frequency, and compare the one or more peak frequencies to a baseline spectrum, wherein a peak frequency present in the converted signal and absent in the baseline spectrum is indicative of a presence of the one or more inhomogeneities in the material sample.

19. A method for detecting one or more inhomogeneities in a material sample, wherein the one or more inhomogeneities have one or more predetermined resonant frequencies, the method comprising:

transmitting, by a pulser-receiver, one or more electrical pulses to a first ultrasound transducer arranged on a first side of the material sample;

generating, by the first ultrasound transducer, one or more one or more high frequency ultrasound (HFU) signals in response to the one or more electrical pulses, wherein the HFU signals propagate through the material sample and undergo scattering;

receiving, by a second ultrasound transducer a second side of the material sample opposite the first side, the one or more scattered HFU signals from the material sample;

transmitting, by the second ultrasound transducer, one or more electronic signals indicative of the one or more scattered HFU signals to a processor via the pulser-receiver;

generating, by the processor, a windowed signal based on the one or more electronic signals by applying a window function;

converting the windowed signal to frequency domain via fast Fourier transform;

determining, for the converted signal, a peak quantity within one or more resonant frequency bands associated with the one or more predetermined resonant frequencies;

wherein the one or more resonant frequency bands comprise a resonant frequency band for each of the one or more predetermined resonant frequencies, wherein each frequency band comprises a frequency bandwidth including the predetermined resonant frequency; and comparing the peak quantity to a baseline value, wherein a peak quantity greater than the baseline value is indicative of a presence of the one or more inhomogeneities in the material sample.

* * * * *